(12) United States Patent
Hussam

(10) Patent No.: US 9,256,645 B2
(45) Date of Patent: Feb. 9, 2016

(54) PATIENT-TO-PATIENT COMMUNITIES

(71) Applicant: Universal Research Solutions, LLC, Columbia, MO (US)

(72) Inventor: Ali Adel Hussam, Columbia, MO (US)

(73) Assignee: Universal Research Solutions, LLC, Columbia, MO (US)

( * ) Notice: Subject to any disclaimer, the term of this patent is extended or adjusted under 35 U.S.C. 154(b) by 191 days.

(21) Appl. No.: 13/968,046

(22) Filed: Aug. 15, 2013

(65) Prior Publication Data

US 2015/0052160 A1    Feb. 19, 2015

(51) Int. Cl.
  *G06F 17/30*    (2006.01)
  *G06F 19/00*    (2011.01)

(52) U.S. Cl.
  CPC ........ *G06F 17/30477* (2013.01); *G06F 19/322* (2013.01); *G06F 19/3425* (2013.01); *G06F 19/3443* (2013.01); *G06F 19/327* (2013.01); *G06F 19/3475* (2013.01)

(58) Field of Classification Search
  CPC .............. G06F 19/3418; G06F 19/345; G06F 19/3443; G06F 19/322; G06F 19/3456; G06F 19/363; G06F 19/3481; G06F 21/6245; G06F 19/3425; G06F 19/3462
  See application file for complete search history.

(56) References Cited

U.S. PATENT DOCUMENTS

| | | | |
|---|---|---|---|
| 6,424,996 B1 * | 7/2002 | Killcommons et al. | 709/206 |
| 7,613,620 B2 | 11/2009 | Salwan | |
| 8,751,257 B2 | 6/2014 | Amland et al. | |
| 2002/0065682 A1 * | 5/2002 | Goldenberg | 705/2 |
| 2003/0061072 A1 * | 3/2003 | Baker et al. | 705/3 |
| 2003/0108849 A1 | 6/2003 | Hodges | |
| 2009/0037470 A1 * | 2/2009 | Schmidt | 707/104.1 |
| 2010/0293170 A1 * | 11/2010 | Hall et al. | 707/750 |
| 2011/0178820 A1 * | 7/2011 | Soni et al. | 705/3 |
| 2012/0072232 A1 * | 3/2012 | Frankham et al. | 705/2 |
| 2012/0173256 A1 | 7/2012 | Kishon et al. | |
| 2012/0182291 A1 * | 7/2012 | Rawat et al. | 345/419 |

FOREIGN PATENT DOCUMENTS

| | | |
|---|---|---|
| WO | WO2011042838 | 4/2011 |
| WO | WO2013098740 | 7/2013 |

* cited by examiner

*Primary Examiner* — Angelica Ruiz
(74) *Attorney, Agent, or Firm* — Fish & Richardson P.C.

(57) ABSTRACT

A computer-implemented method includes receiving a request to search for other users who are associated with at least a threshold level of similarity to the requesting user; accessing information indicative of a patient profile of the requesting user; determining one or more attributes of the requesting user; searching a data repository for information indicative of a user associated with one or more attributes corresponding to at least one of the one or more attributes of the requesting user; identifying, based on searching, a user associated with one or more attributes corresponding to at least one of the one or more attributes of the requesting user; determining that the one or more corresponding attributes of the identified user satisfy the threshold level of similarity; and transmitting information indicative of the identified user, with the transmitted information specifying the identified user as being a peer of the requesting user.

18 Claims, 15 Drawing Sheets

PATIENT-TO-PATIENT COMMUNITIES

BACKGROUND

Social networks and other on-line communities provide different outlets for users of the respective social networks to interact and provide information about what is happening in the life of particular users of the respective social networks.

SUMMARY

In general, an online patient community system is described. A online patient community allows users whom either are contemplating a medical procedure or have already undergone a medical procedure to locate other users that are similarly situated. In an example, a user that has undergone a hip-replacement surgery can locate other users that have undergone the same surgery. The online patient community system also allows users to track their recovery and the recovery of other users. In an example, the online patient community system may allow users to keep a recovery log of their day-to-day progress, which can be shared with other users that are also recovering from similar procedures. Users of the online patient community system can also compare their progress either pre- or post-procedure with the progress of others. In an example, this can include, among other things, a particular user of the online patient community system viewing logs of other users that are progressing more favorably than the particular user so that the particular user may choose to alter their regimen.

In one aspect of the present disclosure, a computer-implemented method include receiving, by a processing device and from a client device associated with a requesting user of an online patient community, a request to search for other users who are associated with at least a threshold level of similarity to the requesting user; accessing information indicative of a patient profile of the requesting user; determining, based on contents of the patient profile, one or more attributes of the requesting user; searching a data repository for information indicative of a user associated with one or more attributes corresponding to at least one of the one or more attributes of the requesting user; identifying, based on searching, a user associated with one or more attributes corresponding to at least one of the one or more attributes of the requesting user; determining that the one or more corresponding attributes of the identified user satisfy the threshold level of similarity; and transmitting, to the client device, information indicative of the identified user, with the transmitted information specifying the identified user as being a peer of the requesting user.

Implementations of the disclosure may include one or more of the following features. In some implementations, the method includes receiving, from the client device, a request to connect the identified user to the requesting user in the online patient community. In other implementations, the method includes receiving, from the client device, information indicative of one or more attributes of the requesting user; and updating the patient profile of the requesting user with the information indicative of the one or more attributes. In still other implementations, the method includes accessing a medical data record of the requesting user; parsing the medical data record; determining, based on parsing, information indicative of one or more attributes of the requesting user; and updating the patient profile of the requesting user with the information indicative of the one or more attributes. In yet other implementations, the method includes receiving, from the client device, information indicative of recovery information of the requesting user; and sharing the received recovery information with peers of the requesting user in the online patient community; wherein the shared recovery information increases a speed of recovery of at least one of the peers of the requesting user, relative to other speeds of recovery that result from other shared information. In still other implementations, the method includes receiving, from the client device, information indicative of one or more of medical information of the requesting user; and sharing the received medical information with peers of the requesting user in the online patient community.

In other implementations, a computer-implemented method includes receiving, by a processing device and from a client device associated with a user of an online patient community, a request to search medical service providers; accessing information indicative of a patient profile of the user; determining, based on contents of the patient profile, one or more symptoms of the user; searching a data repository for information indicative of one or more medical service providers who are qualified to address at least one of the one or more symptoms of the user; identifying, based on searching, a medical service provider who is qualified to address at least one of the one or more symptoms of the user; and transmitting, to the client device, information indicative of the identified medical service provider.

Implementations of the disclosure may include one or more of the following features. In some implementations, the method includes generating data for a graphical user interface that when rendered on display device comprises: a first visual representation of the determined one or more symptoms of the user; a second visual representation of other information included in the patient profile; a control for the user to modify one or more of the determined one or more symptoms and the other information included in the patient profile; an input box for the user to enter information indicative of one or more procedures; wherein searching comprises: searching the data repository for information indicative of one or more medical service providers who are qualified to address at least one of the one or more symptoms of the user and who are qualified to perform at least one of the one or more procedures.

In another aspect of the disclosure, one or more machine readable hardware storage devices store instructions that are executable by one or more processing devices to perform operations comprising receiving, from a client device associated with a requesting user of an online patient community, a request to search for other users who are associated with at least a threshold level of similarity to the requesting user; accessing information indicative of a patient profile of the requesting user; determining, based on contents of the patient profile, one or more attributes of the requesting user; searching a data repository for information indicative of a user associated with one or more attributes corresponding to at least one of the one or more attributes of the requesting user; identifying, based on searching, a user associated with one or more attributes corresponding to at least one of the one or more attributes of the requesting user; determining that the one or more corresponding attributes of the identified user satisfy the threshold level of similarity; and transmitting, to the client device, information indicative of the identified user, with the transmitted information specifying the identified user as being a peer of the requesting user. This aspect may include one or more of the foregoing features.

In still another aspect of the disclosure, an electronic system includes one or more processing devices and one or more machine readable hardware storage devices store instructions that are executable by the one or more processing devices to perform operations comprising receiving, from a client device associated with a requesting user of an online patient community, a request to search for other users who are associated with at least a threshold level of similarity to the requesting user; accessing information indicative of a patient profile of the requesting user; determining, based on contents of the patient profile, one or more attributes of the requesting user; searching a data repository for information indicative of a user associated with one or more attributes corresponding to at least one of the one or more attributes of the requesting user; identifying, based on searching, a user associated with one or more attributes corresponding to at least one of the one or more attributes of the requesting user; determining that the one or more corresponding attributes of the identified user satisfy the threshold level of similarity; and transmitting, to the client device, information indicative of the identified user, with the transmitted information specifying the identified user as being a peer of the requesting user. This aspect may include one or more of the foregoing features.

All or part of the foregoing may be implemented as a computer program product including instructions that are stored on one or more non-transitory machine-readable storage media, and that are executable on one or more processing devices. All or part of the foregoing may be implemented as an apparatus, method, or electronic system that may include one or more processing devices and memory to store executable instructions to implement the stated functions.

The details of one or more implementations are set forth in the accompanying drawings and the description below. Other features, objects, and advantages will be apparent from the description and drawings, and from the claims.

BRIEF DESCRIPTION OF THE FIGURES

FIGS. 2-12 are screen images of graphical user interfaces generated by an application that can be used to interface with the online patient community system.

Like reference symbols in the various drawings indicate like elements.

DETAILED DESCRIPTION

In general, an online patient community system is described in this specification. A user of the online patient community can use the user's profile to build a network of other users, e.g., users with similar profiles. The user can also use the user's profile to search for medical service providers who are qualified to address various medical issues of the consumers.

In an example, an online patient community allows users whom either are contemplating a medical procedure or have already undergone a medical procedure to locate other users that are similarly situated. In an example, a user that has undergone a hip-replacement surgery can locate other users that have undergone the same surgery. The online patient community system also allows users to track their recovery and the recovery of other users. In an example, the online patient community system may allow users to keep a recovery log of their day-to-day progress, which can be shared with other users that are also recovering from similar procedures. Users of the online patient community system can also compare their progress either pre- or post-procedure with the progress of others. This can allow, among other things, a particular user of the online patient community system to view logs of other users that are progressing more favorably than the particular user so that the particular user may choose to alter their regimen.

In general, FIGS. 1-15 are described in relation to the collection and use of certain personal medical information of one or more users. The processes and procedures used by the online patient community system described herein for the collection and use of the personal medical information are compliant with the Health Insurance Portability and Accountability Act (HIPPA) and any other relevant regulations for the protection of personal medical information and other information. In addition, in some implementations, aspects of some or all of the information that is collected by the online patient community system can be anonymized to add additional privacy protections for the users of the online patient community system.

Figure 1:
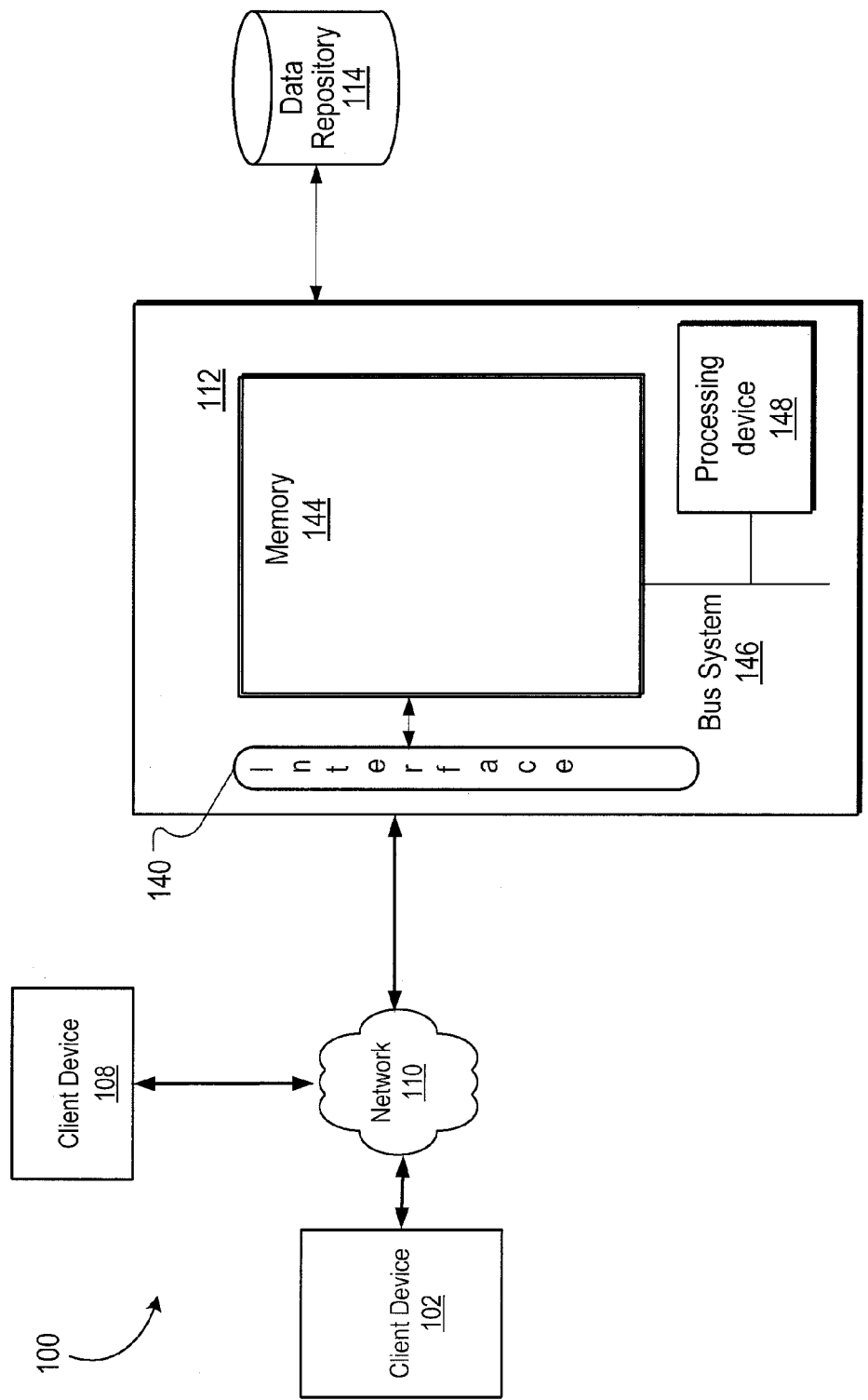
FIG. 1 is a block diagram of components of an online patient community system.

FIG. 1 is a block diagram of components of an online patient community system 100. In FIG. 1, client devices 102, 108 can be any sort of computing devices capable of taking input from a user and communicating over network 110 with server 112 and/or with other client devices. For example, client devices 102, 108 can be mobile devices, desktop computers, laptops, cell phones, personal digital assistants ("PDAs"), servers, embedded computing systems, and so forth.

In an example, the client devices 102 and 108 are configured to present one or more graphical users interfaces to their respective users. In a particular example, the client devices 102 and 108 have been installed with an application or other executable code. The application or executable code can cause presentation of the graphical user interfaces when the application or executable code is executed, e.g., by a processing device 148. These graphical user interfaces allow users to enter information and interact with other users of the online patient community system 100. Particular examples of graphical user interfaces are described in more detail below.

Server 112 can be any of a variety of computing devices capable of receiving data, such as a server, a distributed computing system, a desktop computer, a laptop, a cell phone, a rack-mounted server, and so forth. Server 112 may be a single server or a group of servers that are at a same location or at different locations.

In general, the server 112 can serve as platform for the online patient community system whereby users can connect with each other and share information related to their recovery status. In an example, each of the client devices 102 and 108 can communicate with the server 112 and provide data indicative of a recovery log or other status updates to the server 112.

The illustrated server 112 can receive data from client devices 102, 108 via input/output ("I/O") interface 140. I/O interface 140 can be any type of interface capable of receiving data over a network, such as an Ethernet interface, a wireless networking interface, a fiber-optic networking interface, a modem, and so forth. Server 112 also includes a processing device 148 and memory 144. A bus system 146, including, for example, a data bus and a motherboard, can be used to establish and to control data communication between the components of server 112.

The illustrated processing device 148 may include one or more microprocessors. Generally, processing device 148 may include any appropriate processor and/or logic that is capable of receiving and storing data, and of communicating over a network (not shown). Memory 144 can include a hard drive and a random access memory storage device, such as a dynamic random access memory, or other types of non-transitory machine-readable storage devices. Memory 144 stores computer programs (not shown) that are executable by processing device 148 to perform the techniques described herein.

In an example, server 112 generates and implements the online patient community, e.g., a social networking platform that enables individual users to establish social connections with other users of the social networking platform. The social connections formed between individual users within a social networking platform may be represented in the form of a graph, where users are represented by nodes and social connections between users are represented by edges connecting the nodes. These social connections between users may reflect relationships between the underlying human users who correspond to the users. For example, a social connection between two user identities within the online patient community may reflect a social friendship (e.g., developed through physical interaction in the real-world and/or through on-line interaction in the cyber-world) or a professional relationship between the underlying human users who correspond to the user identities. This social friendship may be based on the two users having similar medical issues, similar prescribed therapies, being interested in similar medical topics, and so forth.

In an example, a user of the online patient community may be able to unilaterally form a social connection with another user of the online patient community, e.g., based on the two users having a same or a similar medical condition. In this example, the online patient community may enable a first user to form a connection to a second user by specifying a desire to form a social connection to the second user and without requiring approval of the connection by the second user. In another example, the formation of social connections between two user may be a bilateral process. In this example, when a first user specifies a desire to form a connection to a second user identity, the online patient community may establish the connection only after the second user approves the formation of the connection between the first user and the second user.

A user of the online patient community may form an online patient community within the social networking platform by forming social connections to other users of the social networking platform. In some cases, the online patient community of a particular user of a social networking platform may be defined as the group of other users to whom the particular user identity is directly connected. Alternatively, in other cases, the online patient community of a particular user of a social networking platform may be defined to include a group of other users that are within a threshold number of degrees of separation of the particular user. In an example, a graph or other data structure may be maintained by the social networking platform to describe the degrees of separation between a particular users and other users.

Referring now to FIGS. 2-12, server 112 can generate information for one or more graphical user interfaces that provide information to a user of the online patient community system 100 (FIG. 1). In general, this information can be indicative of various things to aid the user in making informed decisions with respect to their respective medical care. In an example, the information can be indicative of a profile of one or more users of the online patient community system 100 who have undergone a similar procedure. In another example, the information can be indicative of physicians or other service providers that perform the particular procedure. In yet another example, the information can be indicative of a recovery log for a particular user of the online patient community system 100.

In general the graphical user interfaces can be rendered by an application installed on a client device 102 or 108 (FIG. 1) as part of execution of the application. In an example, the graphical user interfaces can be rendered by an application that when executed generates the graphical user by loading graphical resources stored on the client device 102 or 108 and installed as part of the installation of the application. In another example, the graphical user interfaces can be generated by a browser-based application that generates that graphical user interfaces by receiving and interpreting information indicative of one or more web pages provided by the online patient community system 100.

Figure 2:
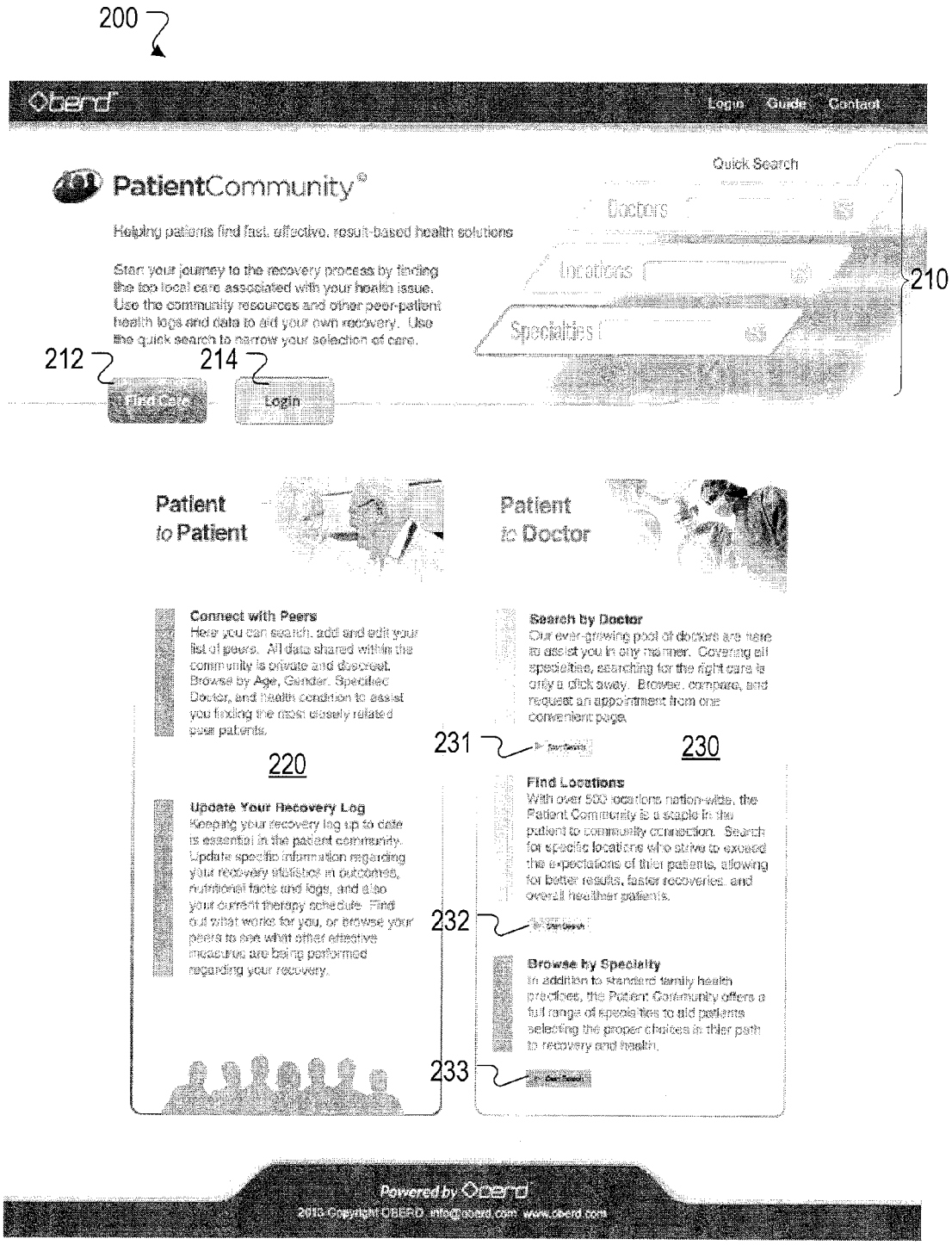

Referring now to FIG. 2, a screen image of a graphical user interface 200 is shown that may be presented as a home screen or other initial landing screen. In an example, the graphical user interface 200 can be presented when a user first executes an application that can interface with the online patient community system 100 (FIG. 1). In another example, the graphical user interface 200 can be presented when a user navigates to a web page that is provided by the online patient community system 100 (FIG. 1) using a browser-based application.

In a particular example, the graphical user interface 200 includes a quick search region 210, a patient-to-patient region 220, and a patient-to-doctor region 230. The particular example of the graphical user interface 200 also includes "find care" user interface control 212 and a "login" user interface control 214.

The quick search region 210 allows a user to enter certain search criteria related to doctors, locations, and specialties into respective fields of the quick search region 210 to identify medical service providers that match the provide search criteria. A user need not enter information into all fields of the quick search region 210 to obtain search results. In an example, a user can search for doctors by last name only without providing a location or a specialty in the quick search region 210. As a result of providing the search criteria, the online patient community system 100 (FIG. 1) can perform a search to locate one or more medical service providers, such as doctors, hospitals, physical therapists, and other medical service provides that are response to the search request.

The patient-to-patient region 220 presents useful information about the online patient community system 100 (FIG. 1) to a user. This may entice or otherwise convince a user to register with the online patient community system 100. In a particular example, the user may register with the online patient community system 100 using he "login" user interface control 214.

In some implementations, when a user selects the "login" user interface control 214, the application may generate another graphical user interface that allows the user to login into the online patient community system using various login credentials. An example of a graphical user interface that can be used for this purpose is described in more detail in reference to FIG. 6.

The doctor-to-patient region 230 presents useful information to users who are searching for medical service providers. In addition, the doctor-to-patient region 230 presents user interface controls 231, 232, and 233 that when selected perform a particular targeted search. In an example, if a user selects the user interface control 231, the user can perform a search to find a specific doctor. In another example, if a user selects the user interface control 232, the user can perform a search to find a specific location in which to have a medical procedure performed.

In some implementations, when a user selects the "find care" user interface control 212, the application may generate another graphical user interface that allows the user to search for search for medical care by providing one or more pieces of information.

Figure 3:
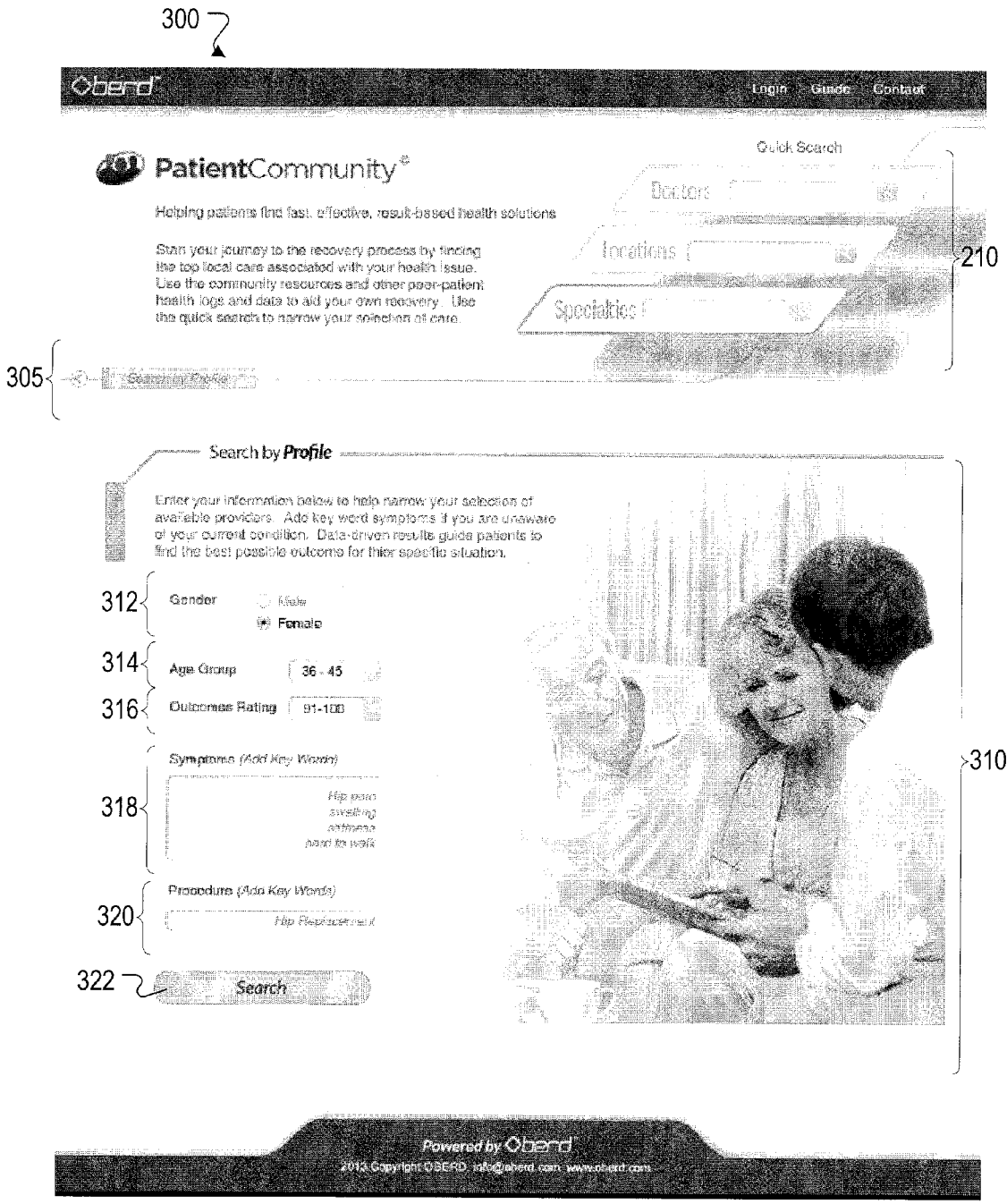
Figure 4:
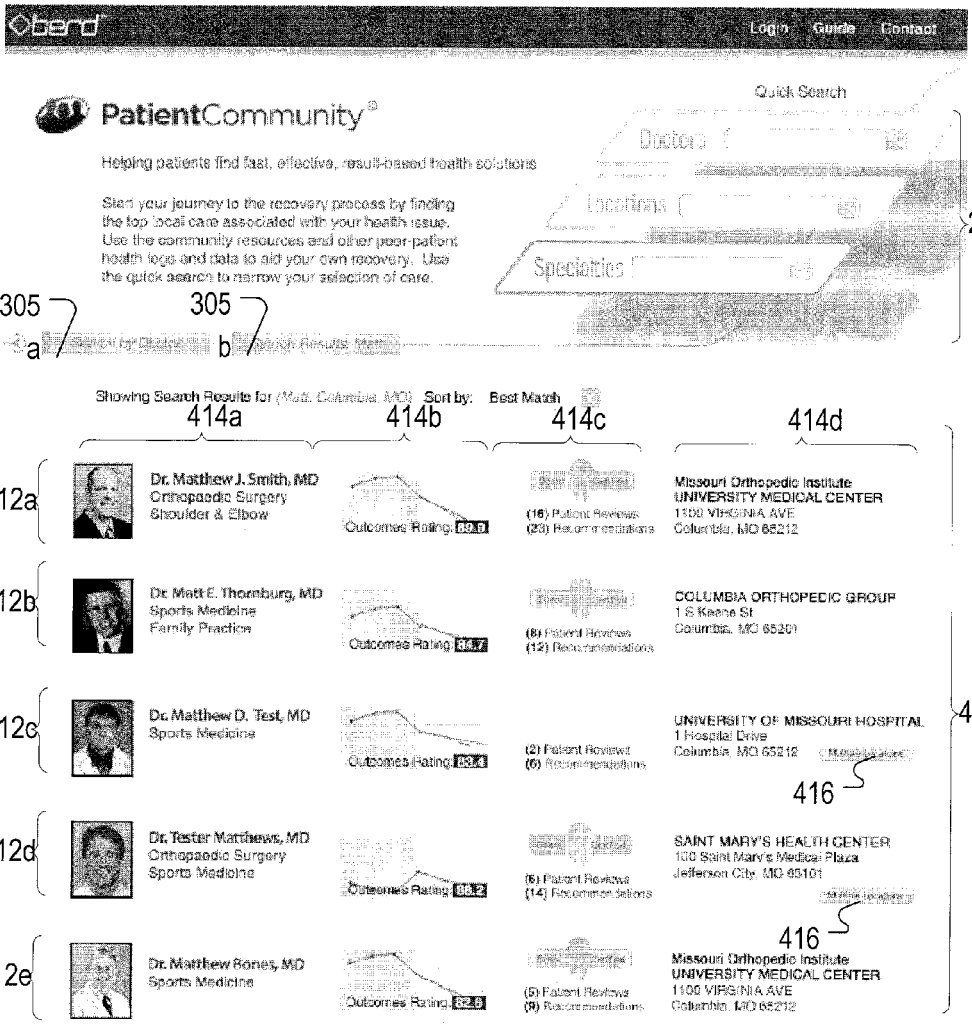
Figure 5:
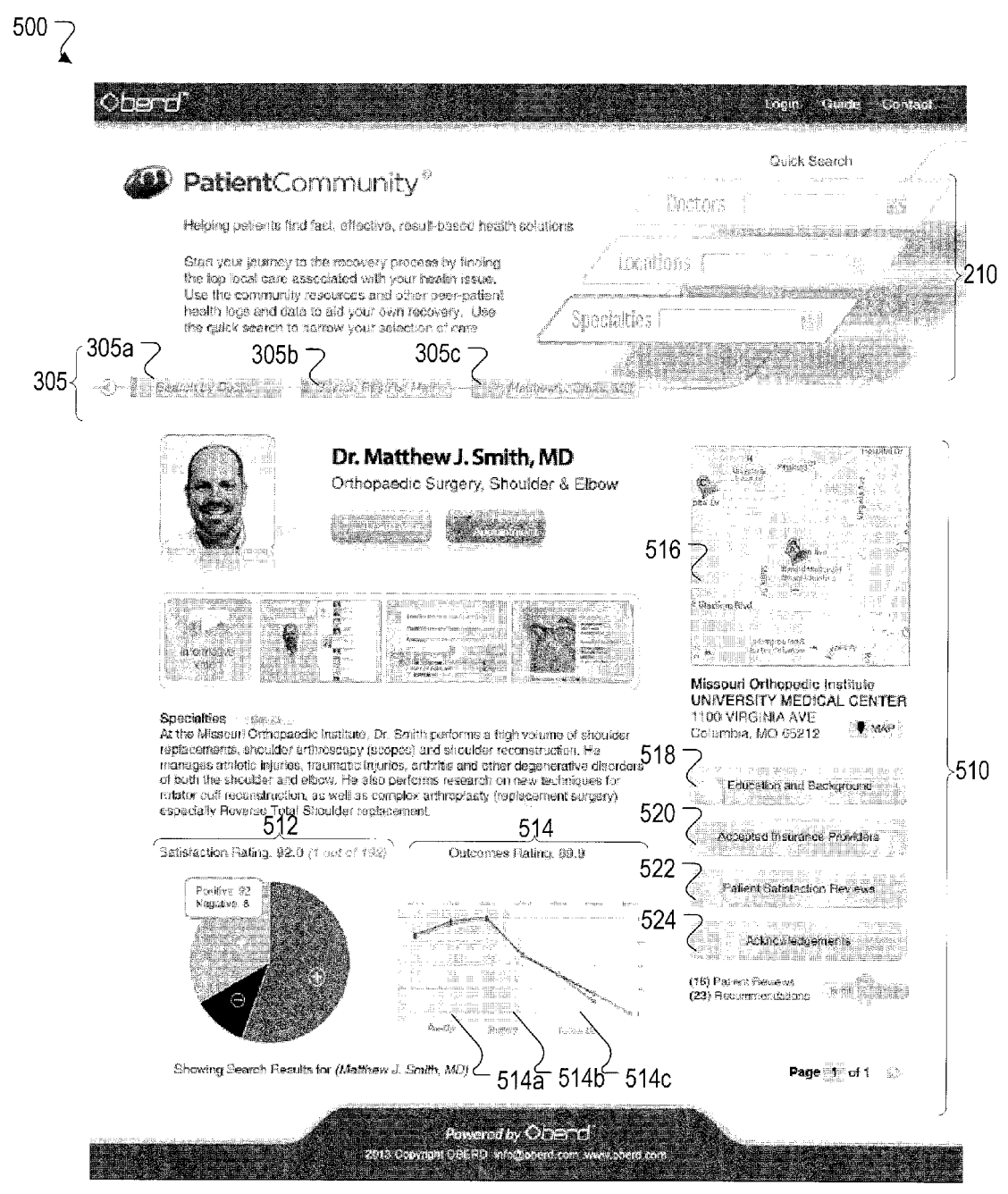

FIGS. 3-5 are now described. In general, FIGS. 3-5 show screen images of graphical user interfaces for an application in communication with the online patient community system 100 (FIG. 1). In a particular example, the graphical user interfaces shown in FIGS. 3-5 illustrate aspects of the online patient community system that pertain the features of the online patient community system 100 that relate to patient-to-doctor searching and communication.

Referring now to FIG. 3, a screen image of a graphical user interface 300 is shown that may be presented to a user allowing the user to perform one or more searches for service providers. The graphical interface 300 includes the quick search region 210, a search activity indicator 305, and a second search region 310.

The search activity indicator 305 can provide one or more user interface elements with respect to a particular user's search activity. The search activity indicator 305 is shown in multiple of the graphical interfaces 300, 400, and 500. In some implementations, when a user selects one of the user interface elements, a respective graphical user interface changes so that a selected activity is presented in a different graphical user interface. Additional examples of the search activity indicator are described in more detail elsewhere in this specification.

The second search region 310 allows the user to perform a more refined search that the quick search region 210 by allowing the user to provide additional information for a particular kind of search to find information for which the user is searching. In the depicted example, the second search region 310 allows a user to search for service providers based on profile information that is stored by the online patient community system 100 (FIG. 1). Examples of providing profile information are described in more detail elsewhere in this specification. In some implementations, the search region 310 may allow for other kinds of searching, such as searching by doctor, searching by location, searching by specialty, and so forth. In general, second search region 310 is populated with various user input controls based on the type of search to be performed.

In an example, because the second search region 310 is being used to search by profile, one or more user input controls 312-320 can be presented to relate to profile information that pertains to one or more users of the online patient community system 100 (FIG. 1). In general, a user can provide input into one or more of the user input controls 312-320 to search the profiles of the users of the online patient community system 100 according to the search criteria provided by the user.

In a particular example, the user input control 314 can be used to search users of the online patient community system 100 based on the respective ages of the users of the online patient community system 100. In other particular examples, a user can provide an outcome rating range into the user input control 316, symptoms into the user input control 318, and procedures into the user input control 320. These and other aspects of profile information stored in the online patient community system 100 are described elsewhere in this specification.

In an example, controls in second search region 310 can be automatically populated with values that are included in a user profile. In this example, server 112, accesses information indicative of a patient profile of the user. Server 112 determining, based on contents of the user profile, one or more symptoms of the user. In this example, server 112 pre-populates user input control 318 with the determined one or more symptoms of the user. In this example, a user profile is being used to drive identification of a medical service provider who is qualified to address at least one of the one or more symptoms of the user. In this example, user input control 318 includes a visual representation of the determined one or more symptoms.

Referring now to FIG. 4, a screen image of a graphical user interface 400 is shown that can be used to provide search results. In a particular example, the graphical user interface 400 provides search results according to a search conducted by a user to identify one or more doctors. A similar interface may also be provided when the search is for other users in the online patient community system 100 (FIG. 1) or other searches such as location searches, specialty searches, and so forth.

In general, the graphical user interface 400 includes the quick search region 210, the search activity indicator 305, and a detailed search results region 410. In the depicted example, the search activity indicator 305 includes user interface elements 305a and 305b. The user interface element 305b represents the current search activity of providing search results. If, for example, a user were to select user interface element 305a, the graphical user interface 400 would change so that a user could provide search criteria, similar to the manner in which a user can provide search criteria using graphical user interface 300.

In general, the detailed search results region 410 can be organized in a table-like fashion to provide information about one or more doctors, where the information is responsive to a search request or other request for information. In a particular example, the detailed search results region 410 includes one or more rows 412a-412e and one or more columns, 414a-414d.

Each of the rows 412a-412e provides information about each of the particular doctors whose information matched or was otherwise responsive to a particular search request or other request for information. Column 414a presents personal information about a particular doctor in each of the respective rows 412a-412e. In an example, the column 414a can present a picture of the doctor, their name, and any of their specialties. In a particular example, column 414a for row 412a indicates that the doctor's name is "Dr. Matthew J. Smith, MD" with specialties in orthopedic surgery and shoulder and elbow surgery.

Column 414b shows a graphical representation of the doctor's outcomes rating. In an example, this can be shown as an overall rating, as a trend, and combinations of these. In addition, in an example, the outcomes rating may be shown for pre-op care, surgical care, and follow-up care. In a particular example, column 414b for row 412 indicates that the doctor's overall outcome rating is 89.9. The outcomes ratings are described in more detail elsewhere in this specification.

Column 414c provides additional user-selectable elements that can be viewed to provide additional information about a particular doctor. In an example, the column 414c can provide links to patient reviews and recommendations. That is, if a user selects a link corresponding to either the patient reviews or the recommendations, the graphical user interface 400 may change to present the selected reviews or recommendations. In addition, the user-selectable elements may include a number that indicates a number of patient reviews or recommendations. In a particular example, column 414c indicates for row 412a that there are 18 patient reviews and 23 recommendations.

Column 414d provides location information about particular doctors. In some implementations, the location information is the particular hospital or clinic where the doctor practices. In other implementations, the location information is a particular group in which the doctor belongs. In these and other implementation, there may be multiple locations in which the doctor practices. In a particular example, were a particular doctor is affiliated with multiple locations, a user interface control 416 can be presented that when selected presents the other locations to the user.

In some implementations, one or more portions of the rows 412a-412e and the columns 414a-414d are user selectable. In response, the graphical user interface 400 may change to present additional information that corresponds to the selection. In a particular example, if a user selects a representation in column 414a, the user interface 400 may change to provide more detailed information about the selected doctor.

In some implementations, the graphical user interface 300 can be a front-end to a process for performing a search. In a particular example, the graphical user interface 300 can be a front-end to a process described in reference to FIG. 15, e.g., when the user selects the "Search" user input control 322.

Referring now to FIG. 5, a screen image of a graphical user interface 500 is shown that can be used to present additional information about a selected doctor. In some implementations, the graphical user interface 500 can be shown when a user selects elements of the detailed search region 410 (FIG. 4), such as particular columns 414a-414d in any of the rows 412a-412e. In general, the graphical user interface includes the quick search region 210, the search activity indicator 305, and a doctor information region 510.

In the depicted example, the search activity indicator 305 includes user interface elements 305a, 305b, and 305c. The user interface element 305c represents the current search activity of providing additional information about the selected doctor. If, for example, a user were to select the user interface element 305a, the graphical user interface 500 would change so that a user could provide search criteria, similar to the manner in which a user can provide search criteria using graphical user interface 300.

Similarly, if the user where to select the use interface element 305b, the graphical user interface 500 would change so that a user could review particular search results, similar to the manner in which the user can review search results using graphical user interface 400.

The doctor information region 510 includes information about the selected doctor. In a particular example, the doctor information region 510 can include a picture of the doctor, a description of the doctor's particular specialties, a satisfaction rating indicator 512, an outcome rating indicator 514, a map region 516, and one or more additional components 518-524 that can be selected to provide additional information about the doctor.

The satisfaction ratings indicator 512 can show how particular patients have rated the particular doctor. In a particular example, the satisfaction rating indicator 512 is a graph or chart this includes positive ratings, negative ratings, and neutral ratings. In addition, these positive ratings, negative ratings, and neutral ratings can be used by the online patient community system 100 (FIG. 1) to compute an over satisfaction rating for the particular doctor. Various techniques can be used by the online patient community system 100 to determine the overall rating of the doctor, including computing an average rating based on one or more rating scores provided by users of the online patient community system 100.

The outcome ratings indicator 514 may be similar to the information presented in column 414b of the detailed search results region 410 (FIG. 4). In some implementations, the outcome ratings indicator 514, however, may be enlarged or include additional information not able to be presented in the detailed search results region 410. In the depicted example, the outcome ratings indicator 514 presents an average outcome rating. In general, an outcome rating is based on some amount of information provided by a physician about an expected outcome and determining whether the actual outcome was in-line with the expectations. In an example, the outcome rating is based on a collection of patient outcome-based data. Generally, patient outcome-based data includes data collected by the online patient community system 100 (FIG. 1) to evaluate the capacity of a medical procedure and/or process to function at a pre-defined level. In a particular example, if a procedure has average recovery of 8 weeks, the outcome rating can be based on a number of patients that are treated by the particular doctor that recover more quickly than average, recovery less quickly than average, and recover on average with the pre-defined recover level.

In some implementations, the outcome ratings can be sub-divided into pre-op expectation ratings 514a, surgical expectation ratings 514b, and follow-up expectation ratings 514c. In an example, the outcome rating can be based different ratings for each of pre-op expectation ratings 514a, surgical expectation ratings 514b, and the follow-up expectation ratings 514c.

The map region 516 can present a location of doctor in a surrounding area. In some implementations, the map region 516 can be zoomed-in or zoomed-out to provide addition views of the location and surrounding area. The one or more additional components 518-524 that can be selected by user based on the wanting to view other information about the doctor. As an example, the user can select the additional component 518 to view more information about the doctor's education and background based on information that is stored on the online patient community system 100 (FIG. 1).

FIGS. 6-12 are now described. In general, FIGS. 6-12 show screen images of graphical user interfaces for an application in communication with the online patient community system 100 (FIG. 1). In a particular example, the graphical user interfaces shown in FIGS. 6-12 illustrate aspects of the online patient community system that pertain the features of the online patient community system 100 that relate to patient-to-patient searching, communication, and other patient-to-patient community-based features.

Figure 6:
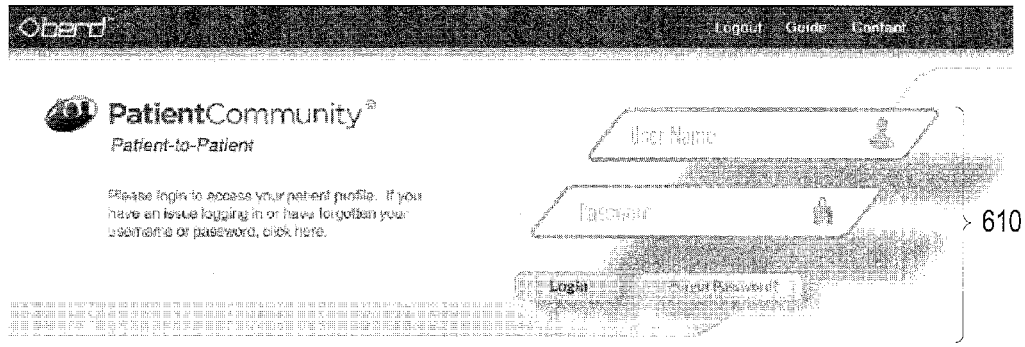
Figure 6:
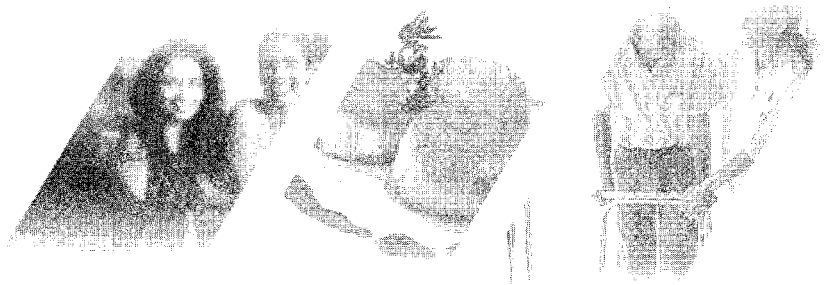
Figure 6:

Referring now to FIG. 6, a screen image of a graphical user interface 600 is shown that can be used as a login page, landing page, or other home page for a patient-to-patient community hosted by the online patient community system 100 (FIG. 1). In general, the graphical user interface 600 includes a user credential region 610 that allows a user to provide at least a username and password. The online patient community system 100 can verify the provided username and password to grant access to the patient-to-patient community hosted by the online patient community system 100.

Figure 7:
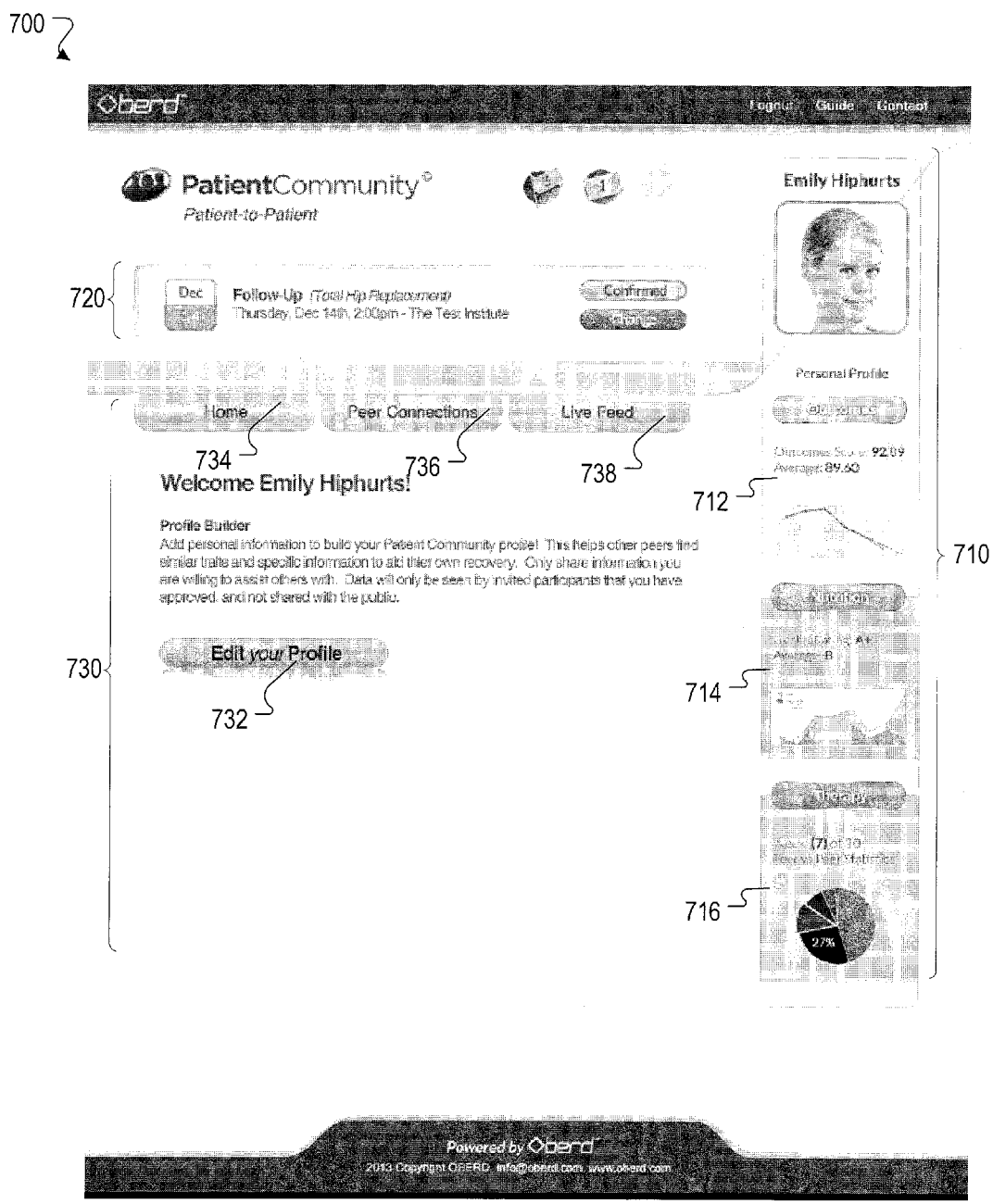

Referring now to FIG. 7, a screen image of a graphical user interface 700 is shown that can be used as a welcome page and/or profile page for a particular user of the patient-to-patient community host by the online patient community system 100 (FIG. 1). In an example, the graphical user interface 700 can be presented to a user once the online patient community system 100 has verified the username and password provided the user in the user credential region 610 (FIG.

6). In general, the graphical user interface 100 provides one or more graphical user components that allow a user to manage their patient profile on the online patient community system 100, track their recovery progress relative to other users of the online patient community system 100, and search for other user of the online patient community system 100 based on similar procedures performed or other search criteria, to name few examples. In a particular example, the graphical user interface 700 includes a profile region 710, an appointment region 720, and an information region 730.

The profile region 710 includes graphical representations indicative of certain information about a particular user's recovery or general health. In a particular example, the profile region 710 includes a picture of the user, an outcome score region 712, a nutrition region 714, and a therapy region 714. In general, the graphical representatives in the profile region 710 are indicative of different aspects of the user's recovery that are determined from information that the particular user enters into a recovery log or other aspect of the particular user's profile. Entering information about aspects of the particular user's profile is described in more detail elsewhere in this specification.

In general, the outcome score region 712 includes an outcome score for one or more procedures that the particular user has undergone. In some implementations, the outcome score region 710 may be subdivided into a pre-op outcome score region, a surgery outcome score region, and a follow-up outcome score region, similar to the subdivisions described in reference to FIG. 5. In an example, the outcome score presented in the outcome score region 712 for the particular user can be based on their respective progress relative to all other users of the online patient community system 100 that have undergone a similar procedure. In another example, the outcome score presented in the outcome score region 712 for the particular user can be based on their respective progress relative to only those users of the online patient community system 100 to which the users are acquainted or otherwise connected, e.g., through a friending processes or other similar process that is supported by social networks in general. A particular example of connecting with other users of the online patient community system 100 is described in more detail elsewhere in this specification.

In general, the nutrition and health region 714 includes an indication of the particular user's health rating. In some implementations, the health rating can be based on nutrition information that is entered by the user and compared with a nutritional database and/or compared to one or more users of the online patient community system 100 (FIG. 1). In an example, the health rating presented in the nutrition and health region 714 for the particular user can be based on their respective health and nutrition information relative to all other users of the online patient community system 100 that have undergone a similar procedure. In another example, the health rating presented in the nutrition and health region 714 for the particular user can be based on their respective health and nutrition information relative to only those users of the online patient community system 100 to which the users are acquainted or otherwise connected, e.g., through a friending processes or other similar process that is supported by social networks in general.

In general, the therapy region 716 includes an indication of the particular user's progress in a therapy regimen. In general, the indication can be based on the particular user's current timetable with respect to their medical procedure. In an example, the therapy regimen may be a pre-operative regimen. In another example, the therapy regimen may be a post-operative regimen. In some implementations, the indication in the therapy region 716 can be based on a calendar other appointment schedule that a user of the online patient community system 100 (FIG. 1) can provide physical therapy appointments. In a particular example, the therapy region 716 indicates that the particular user of the online patient community system 100 is on their seventh week of a ten-week therapy regimen. In some implementations, the therapy region 716 also provides a user interface component that allows a particular user to track or otherwise compare their respective therapy progress relative to other users of the online patient community system 100. In an example, therapy comparison for the particular user can be based on their respective progress relative to all other users of the online patient community system 100 that have undergone a similar procedure and/or therapy regimen. In another example, the comparison for the particular user can be based on their respective progress relative to only those users of the online patient community system 100 to which the users are acquainted or otherwise connected, e.g., through a friending processes or other similar process that is supported by social networks in general.

In general, the appointment region 720, can allow a particular user to track important or other relevant appointments relative to a user's medical care. In general, the appointment region 720 may be populated with information that is collect from the user or on behalf of the user. In an example, the appointment region 720 may be populated by referencing medical information stored on a computer at a hospital or other location in which the online patient community system 100 can communicate. In another example, the appointment region 720 may be populated with information that is entered by the particular user, e.g., in a recovery log or other aspects of the particular user's profile. In some implementations, the appointment region 720 allows a user to confirm or change a particular scheduled appointment using various user interface components.

In general, the information region 730 presents information to the particular user that is indicative of various aspects of their user profile. In addition, the information region 730 may provide one or more user interface components that allows a particular user to enter information that pertains to the particular user's recovery.

In an example, the information region 730 includes a profile edit button 732 and one or more selectable user interface tabs 734, 736, and 738. In general, the profile edit button 732 allows the particular user to make changes to their respective profile information. In general, the one or more selectable user interface tabs 734, 736, and 738 that allow a user to present different information in the information region 730 and perform various activities that edit or otherwise affect the contents of the user's profile. Editing profile information and performing a number of other activities are described elsewhere in this specification.

Figure 8:
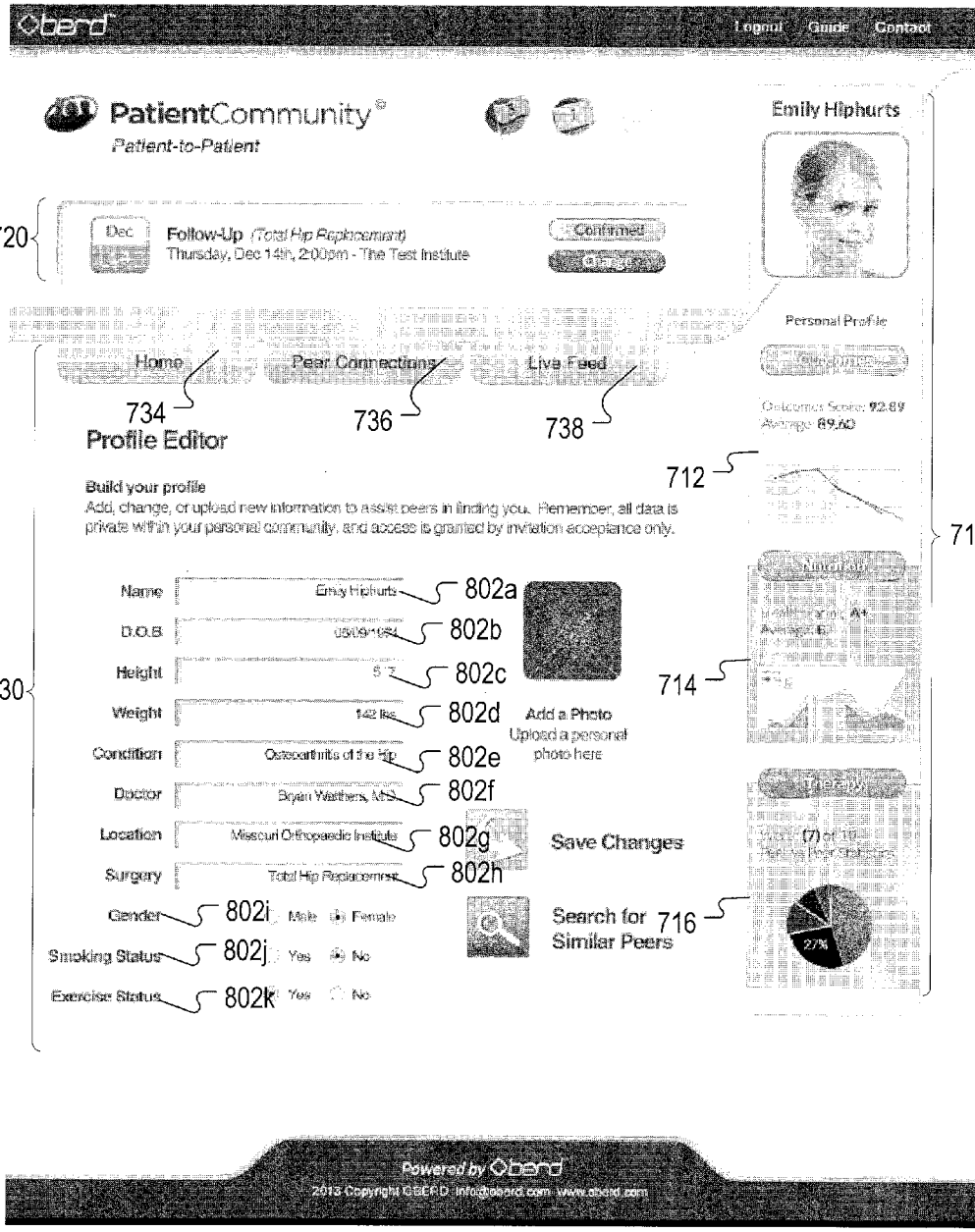

Referring now to FIG. 8, a screen image of a graphical user interface 800 is shown that can be used to edit profile information for a particular user of the online patient community system 100 (FIG. 1). In an example, the graphical user interface 800 can be shown when a user selects the profile edit button 732 shown in FIG. 7. In an example, the information region 730 can present multiple user interface elements that allow a user to modify and update his/her profile information. In a particular example, the information region 730 can present user interface components that allow the particular user to change his/her name, certain demographic information, such as date of birth, gender, location, and so forth, and certain relevant health information, such as exercise status, smoking status, and so forth. In another example, the information region 730 can also present a user interface component that allows a user to add a photo, save changes, or search for similar users (e.g., peers) on the online patient community system 100 (FIG. 1). In an example, server 112 receives, from a client device of a user who is updating a user profile, information indicative of one or more attributes of the user. In the example of FIG. 8, these attributes includes attributes 802a-802k. In this example, server 112 updates the patient profile of the requesting user with the information indicative of the one or more attributes 802a-802k.

In general, the graphical user interface 800 can be used to build a user profile that pertains to a recovery from a medical procedure. In some implementations, other users of the online patient community system 100 (FIG. 1) can use the information that is provided on a particular user's profile to track the progress of the particular user and to see what actions the particular user has taken to achieve a better outcome, e.g., based on a determined outcome score. In some situations, the ability to track another user's progress of the online patient community system may prompt other users to bring to their respective physicians' attention actions that the particular user performed to determine whether those actions may yield a better outcome.

Figure 9:
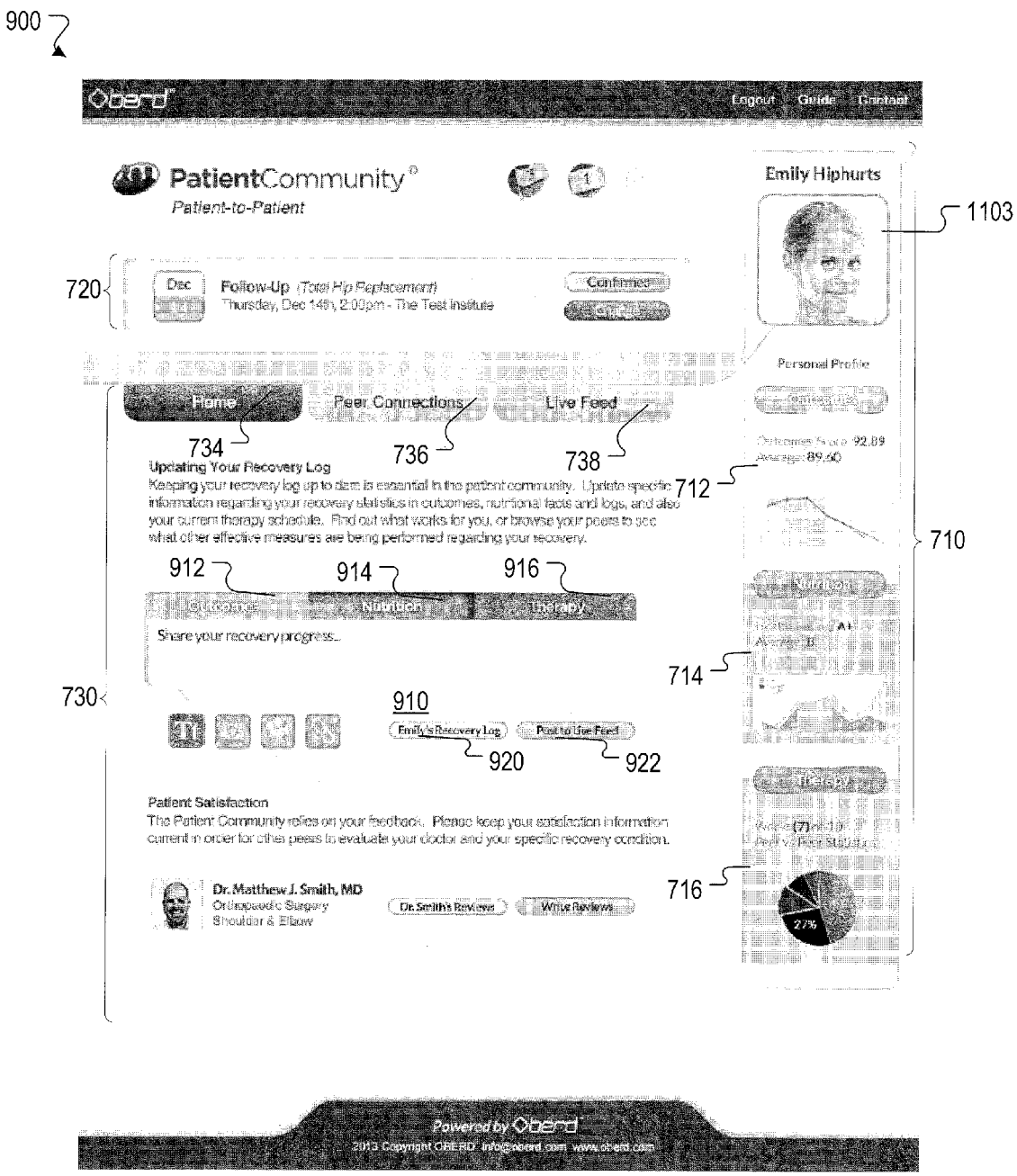

Referring now to FIG. 9, a screen image of a graphical user interface 900 is shown that can be used to by a particular user to provide information about their respective recovery. In general, the graphical user interface 900 can be shown in response to a user selecting the "Home" user interface tab 734. In an example, the user may add or modify their recovery log. As another example, the user may write a review or otherwise rate their physician or others involved in providing medical care to the particular user The graphical user interface 900 includes an edit region 910 that allows a user to make changes to their recovery log. In an example, the edit region 910 can include one or more user interface tabs 912, 914, and 916 that allow a user to edit their recovery log with respect to procedure outcomes, nutrition, and therapy, respectively.

In this example, information in the outcomes tab 912 may be shared with other users who share a social connection to user 1103 in the online patient community. Generally, outcome information includes information indicative of an outcome (e.g., a result) of a pre-operative condition, an operative procedure and/or a post-operative procedure. Through sharing of the outcome information, other users that are connected to user 1103 may read and review the outcome experiences of user 1103. These other users may be similar users to user 1103, e.g., by having similar medical operations and conditions.

In this example, information in the nutrition tab 914 may be shared with other users who share a social connection to user 1103 in the online patient community. Generally, nutrition information includes information indicative of dietary goals and nutrition supplements and other nutrition information of a user. Through sharing of the nutrition information, other users that are connected to user 1103 may read and review the nutrition information of user 1103. These other users may be similar users to user 1103, e.g., by having similar medical operations and conditions. By viewing the nutrition information of user 1103, the other users may ascertain effective nutrition for a medical condition of the other users that is also experienced by user 1103.

In this example, information in the therapy tab 916 may be shared with other users who share a social connection to user 1103 in the online patient community. Generally, therapy information includes information indicative of therapy goals, exercise and programs of a user. Through sharing of the therapy information, other users that are connected to user 1103 may read and review the therapy information of user 1103. These other users may be similar users to user 1103, e.g., by having similar medical operations and conditions. By viewing the therapy information of user 1103, the other users may ascertain what therapies user 1103 has determined to be effective for a medical condition and whether these therapies may also be effective for the other users.

The edit region 910 also includes graphical user elements that can allow the user to control the manner in which the updated recovery log information is stored by the online patient community system 100 (FIG. 1) or presented to other users of the online patient community system 100.

In an example, a use interface component 920 allows user 1103 to save changes to their respective recovery log. In this example, the recovery log may be shared with other users who share a social connection to user 1103 in the online patient community. Through sharing of the recovery log, other users that are connected to user 1103 may read and review the recovery experiences of user 1103. These other users may be similar users to user 1103, e.g., by having similar medical operations and conditions. The shared recovery information of user 1103 increases a speed of recovery of at least one of the peers of user 1103, relative to other speeds of recovery that result from other shared information.

In another example, a user interface component 922 allows a user to post their recovery log information to a live feed. In general, a live feed is real-time feed that shows current user activity with respect to their recovery. In an example, if a particular user is participating in a therapy session, the user can post the appointment to their live feed at the time they begin so that other users can see that the particular user is currently in therapy. Live feed are also described elsewhere in this specification.

Figure 10:
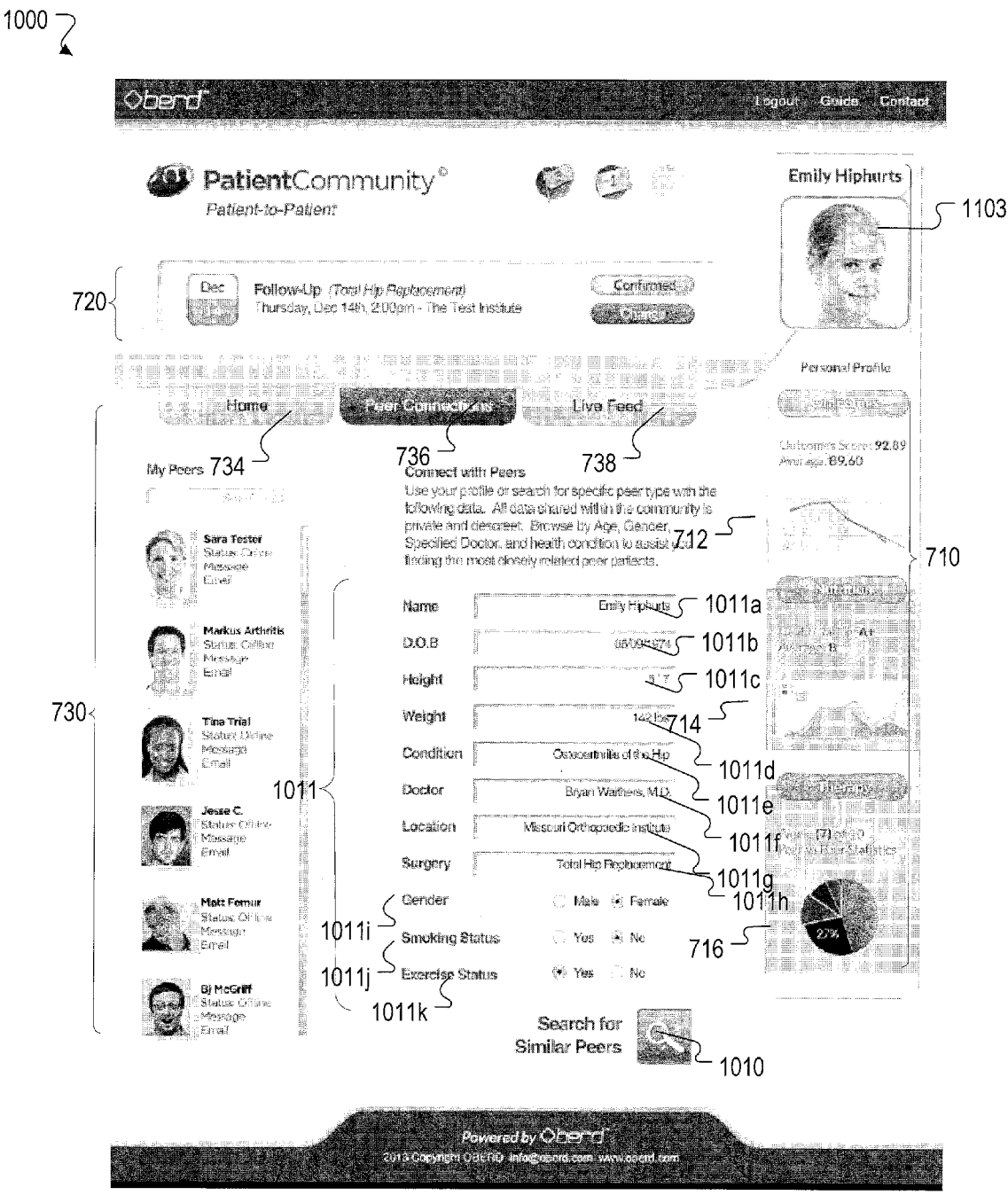

Referring now to FIG. 10, a screen image of a graphical user interface 1000 is shown that can be used to find other users in the online patient community system 100 (FIG. 1) that share one or more characteristics with the particular user. In general, the graphical user interface can be presented in response to a user selecting the "Peer Connection" user interface tab 736.

In general, the shared characteristics that be used to search for other users of the online patient community system 100 (FIG. 1) can be aspects of the one or more user's respective profiles. In an example, users can be matched based on procedures performed, or to be performed, on the respective user, similar age ranges, health ratings, or other information that is associated with or computed from a particular user's profile.

In a particular example, the information region 730 can include one or more user interface components that can list information from the user profile including the name, date of birth, height, weight, medical condition, treating physician, location of the procedure, procedure to be performed, gender, smoking status, exercise status, and other information. In some implementations, the information presented in the information region 730 is automatically populated by referencing medical data maintained by the online patient community system 100 (FIG. 1). For example, data repository 114 may store a medical data record of user 1103. Data repository 114 may originally access the medical data record from an external health care system. Server 112 accesses, from data repository 114, a medical data record of requesting user 1103. Server 112 parses the medical data record. Server 112 determines determining, based on parsing, values of one or more of attributes 1011a-1011k of user 1103. Server 112 updates and/or pre-populates user profile 1011 with the determined values of attributes 1011a-1011k.

In some implementations, the user interface components in the information region 730 can be user-editable, allowing a particular user to enter some or all of the relevant information for which the particular user wishes to base user matches. In some implementations, when a user is satisfied with the profile information presented in the information region 730, the user can select the search button 1010 indicating that the online patient community system 100 should perform a search to find relevant (e.g., similar) other user of the online patient community system 100. In this example, server 112 uses the user profile shown in graphical user interface 1000 to search for similar users, e.g., users with a predefined level of similarity to the user associated with the user profile shown in graphical user interface 1000.

In the example of FIG. 10, information region 730 includes user profile 1011. In this example, user profile 1011 includes information indicative of attributes of a user, including, e.g., attributes 1011a-1011k. Generally, an attribute includes a characteristic of a user and may include a medical condition of a user and/or a medical treatment of the user. Upon selection of search button 1010, server 112 searches for other users that are similar to the user associated with profile 1011. In this example, server 112 searches for these similar users by comparing attributes 1011a-1011k in profile 1011 to attributes in other users profiles, e.g., that are stored in data repository 114. In this example, server 112 identifies a similar user as being a user that is associated with a profile that includes an attribute matching at least one of attributes 1011a-1011k in profile 1011. When server 112 identifies this similar user, server 112 enables the user associated with profile 1011 to become connected to this similar user, e.g., by generates a social connection in the social networking platform of the online patient community between the similar user and the user associated with profile 1011.

Figure 11:
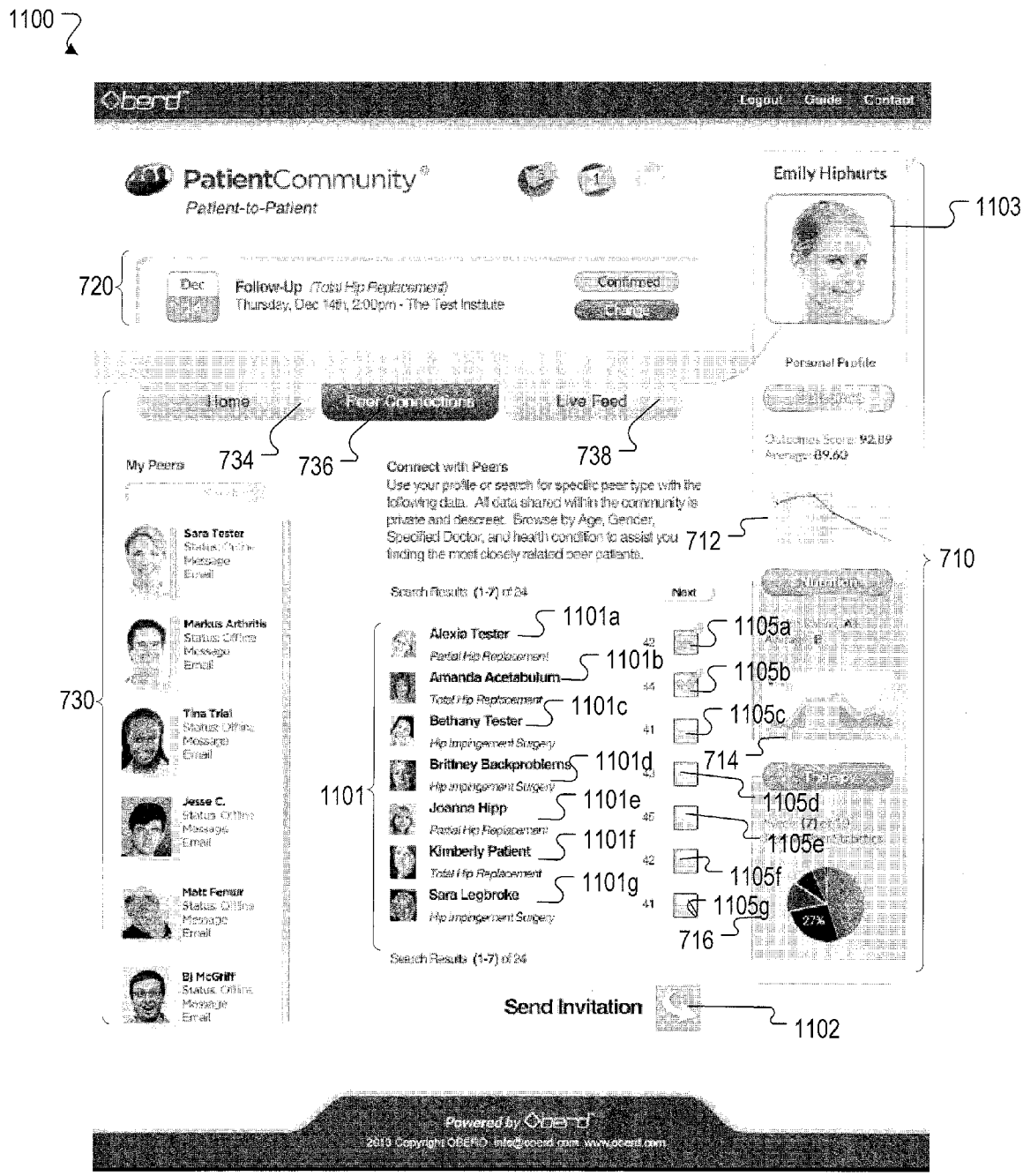

Referring now to FIG. 11, a screen image of a graphical user interface 1100 is shown that can be used to present search results of other peers, or patients, that have profiles on the online patient community system 100 (FIG. 1) and that are responsive to search criteria. In general, the search criteria are provided by the user in the one or more user interface components presenting in the information region 730 of the graphical user interface 1000 (FIG. 10). In addition, in general, the search results may be provided when a user selects the search button 1010 shown in the information region 730 of the graphical user interface 1000.

In the example of FIG. 11, information region 730 includes similar user region 1101 that displays information indicative of similar users 1101a-1101g. In this example, similar users 1101a-1101g are associated with profiles that includes one or more attributes that correspond to (e.g., match) at least one of the attributes of user 1103 who is associated with profile 1011 (FIG. 10). In this example, server 112 uses the profiles of users of the online patient community in identifying similar users.

Referring back to FIG. 10, attribute 1011h of profile 1011 specifies that user 1101 has had a surgical procedure of a total hip replacement. Referring now to FIG. 11, similar users 1101a-1101g each are associated with an attribute that includes a value of "hip," including, e.g., partial hip replacement, total hip replacement and hip impingement surgery. That is, similar users 1101a-1101g are similar to user 1103 because both similar users 1101a-1101g and user 1103 have had medical treatments and/or operations pertaining to the hip. Accordingly, server 112 determines that user 1103 may be interested in tracking treatments and recovery of one or more of similar users 1101a-1101g.

In this example, similar user region 1101 includes invitation controls 1105a-1105g. Each of invitation controls 1105a-1105g are selectable, e.g., to specify that user 1103 wants to invite one or more of similar users 1101a-1101g to be connected to user 1103 in the online patient community. In this example, user 1103 selects invitation controls 1105a, 1105b to invite similar users 1101a, 1101b to become connected with user 1103 in the online patient community. Graphical user interface 1100 includes control 1102, selection of which invites selected similar users (e.g., similar users 1101a, 1101b) to become connected to user 1103 in the online patient community. In this example, server 112 invites selected similar users (e.g., similar users 1101a, 1101b) to become connected to user 1103 in the online patient community by transmitting to client devices used by the selected similar users an email message or text message or other notification message that notifies the selected similar users that user 1103 would like to form a connection in the online patient community. In this example, the notification message includes a selectable link that a similar user can select to send to server 112 a message indicating that the similar user accepts the request to form the connection to user 1103 in the online patient community.

Figure 12:
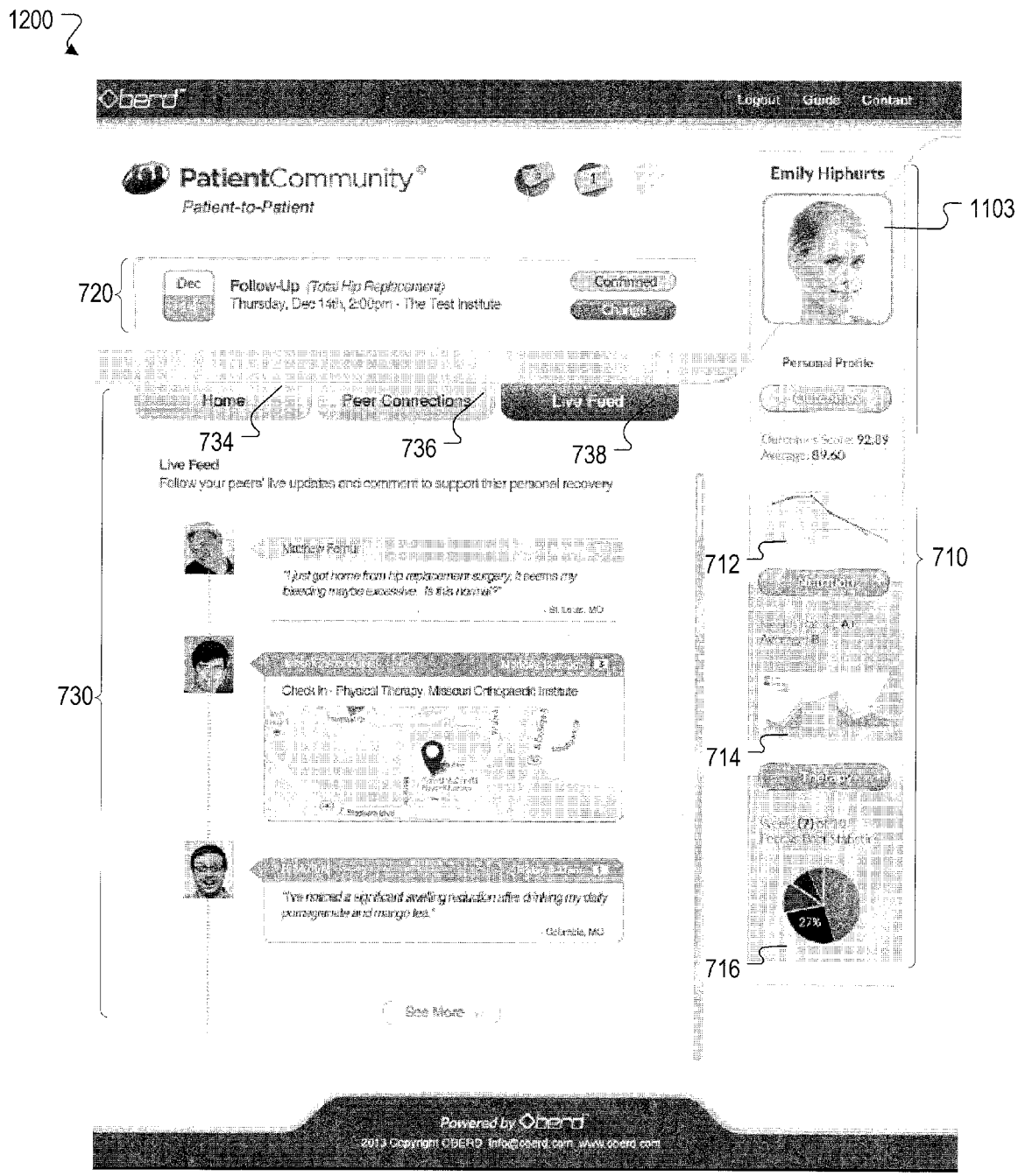

Referring now to FIG. 12, a screen image of a graphical user interface 1200 is shown that can be used to present a live feed. In general, the live-feed can be presented in response to a user selecting the "Live Feed" user interface tab 738. The live feed can provide real-time and pseudo-real-time updates to the particular user that pertain to other users (e.g., similar users) that the particular user is connected to vis-à-vis the online patient community system 100 (FIG. 1). In general, these updates pertain to medical progress of the respective similar users, e.g., to promote user 1103 in learning from treatments and recovery methods of similarly situated users. In an example, a first user can post a question to the live feed about their recovery and have that question answered by other users that are connected to the first user. As another example, a second user can post an update to the live feed about nutritional supplement that has a positive effect on their recovery.

Thus, users of the online patient community system 100 (FIG. 1) can use the live feed to get real-time and pseudo-real-time updates about other users' recoveries and make more informed decisions about actions that the particular users can take to improve the outcomes of their respective procedures. In an example, a particular user can see improvements to multiple other users' outcomes based on a particular nutritional supplement or therapeutic regimen. If the user believes that these improvements are a function of the supplements or therapeutic regimen, they can choose to take that information to their physician so that the particular user and the physician can determine if that course of action may improve the overall outcome.

In some implementations, the live feed presented in the information region 730 can be color-coded. In an example, a first color can be used to represent an update pertaining to an outcome, a second color can be used to represent an update pertaining to nutritional information, and a third color can be used to represent an update pertaining to a therapy session.

Figure 13:
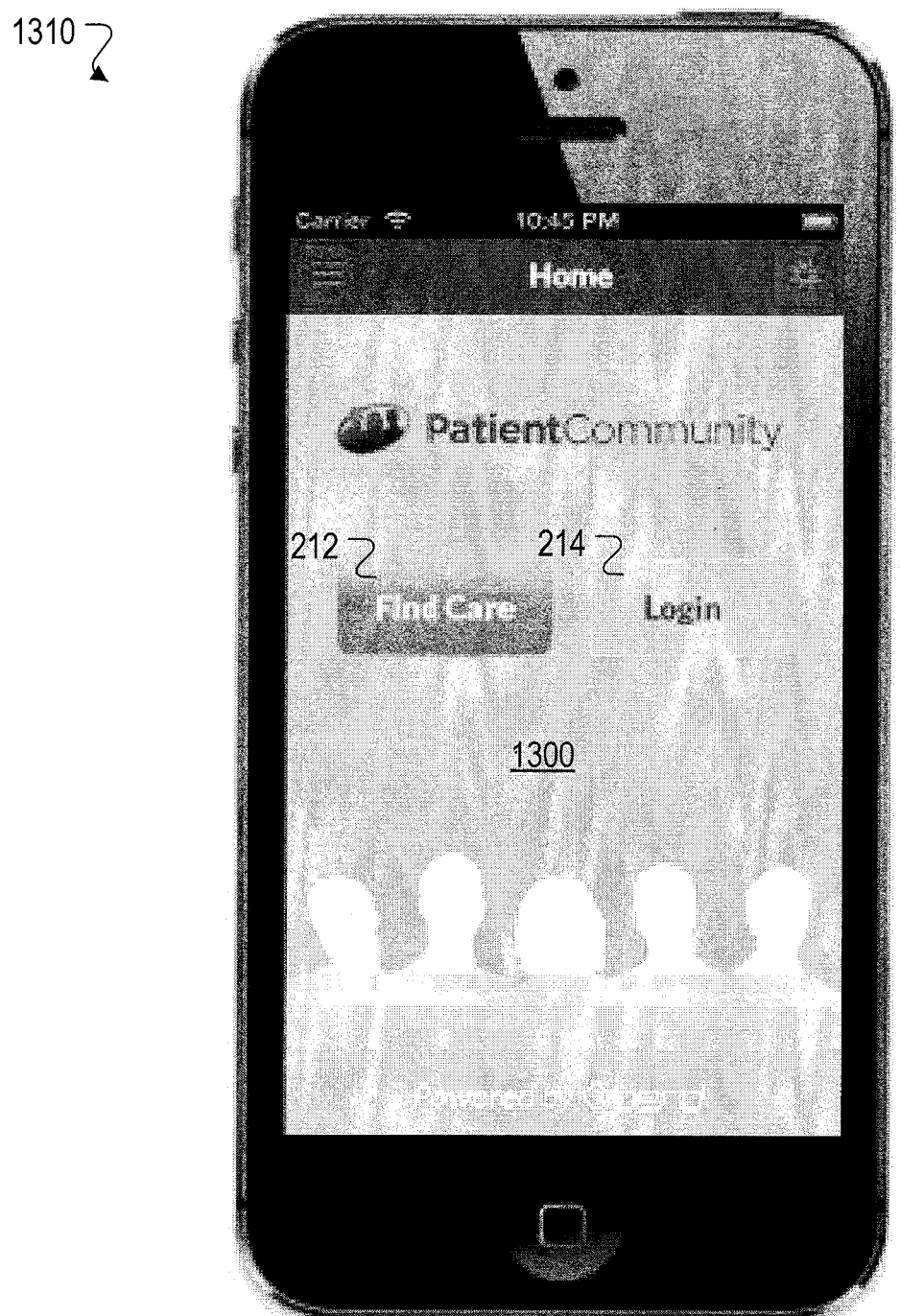
FIG. 13 shows a hand held device executing an application that generates the graphical user interfaces that can be used to interface with the online patient community system.

Referring now to FIG. 13, a screen image of a graphical user interface 1300 is being shown as part of an application loaded on a client device 102 or 108, such as a handheld device 1310. In the depicted example, the graphical user interface 1300 is similar to the graphical user interface 200 that provides a landing screen or home screen to a particular application that can be used to communicate with the online patient community system 100 (FIG.). The graphical user interface 1300, however, may be customized to fit a smaller screen of the handheld device 1310 relative to other client device 102 or 108, such as a desktop computer, laptop computer, and so forth.

In addition, if a user selects either of the "find care" user interface control 212 or the "login" user interface control 214, the application can present additional graphical user interfaces described elsewhere in this specification that satisfy the user selection. In an example, if a user selects the "login" user interface control 214, the user may be presented with a graphical user interface that is similar to the graphical user interface 600 (FIG. 6). In some implementations, however, the user interface may also be customized to fit a small screen of the handheld device 1310.

Figure 14:
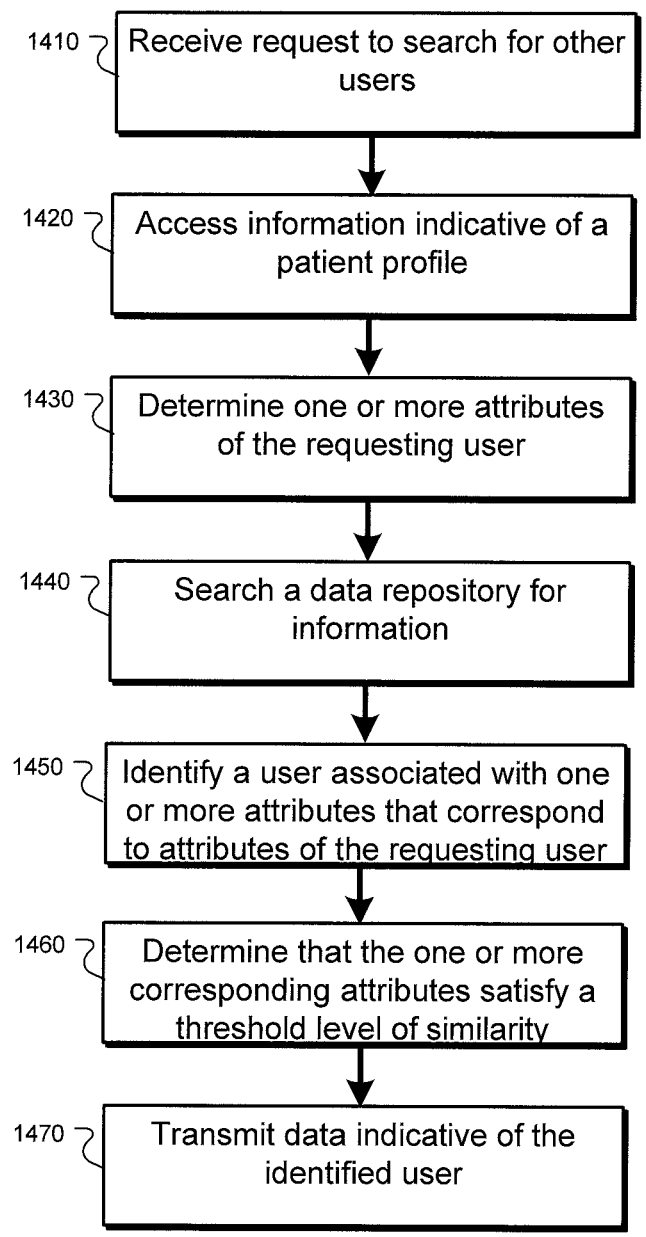
FIG. 14 is a flow chart is a flow chart of an example process that can be used to identify one or more peers to a requesting user of the online patient community system.

FIG. 14 is a flow chart of an example process 1400 that can be used to identify one or more peers to a requesting user of the online patient community system 100 (FIG. 1). Server 112 implements process 1400. In general, the process 1400 determines a threshold (e.g., a predefined amount_level of similarity between a requesting user and other users of the online patient community system 100. In some implementations, the threshold level of similarity can be based at least in part on information that is included in the respective user profiles, e.g., that pertains to a medical condition, procedure, or recovery. In general, process 1400 is described in relation to an online patient community system 100 that is configured to perform the process 1400, although other systems may be configured to perform process 1400.

In operation, server 112 receives (1420) a request to search for other users who are associated with at least a threshold level of similarity to a requesting user. In an example, the online patient community system 100 may receive a request from client devices 102 or 108 that have been installed with an application or program code that can receive user input and transmit that user input in the form of a search request.

Server 112 access (1420) information indicative of a patient profile of the requesting user. In an example, profile information stored by the online patient community system 100 (FIG. 1) can be accessed. In some implementations, this profile information may include recovery log information, nutritional information, therapeutic progress information, and other information that can be used to construct a user profile as described elsewhere in this specification.

Based on contents of the patient profile, server 112 determines (1430) one or more attributes of the requesting user. In an example, the requesting user's medical condition or scheduled procedure may be determined from the patient profile.

Server 112 searches (1440) a data repository for information indicative of a user associated with one or more attributes corresponding to at least one of the one or more attributes of the requesting user. In an example, the online patient community system 100 (FIG. 1) may maintain a database or other data repository that can be searched for information indicative of a user that has a similar medical condition to that of the requesting user or has undergone or is schedule to undergo the same medical procedure as the requesting user.

Server 112 identifies (1450) a user associated with one or more attributes corresponding to at least one of the one or more attributes of the requesting user based on the searching. In an example, users that have a same or similar medical condition to that of the requesting user may be identified. As another example, users that have undergone or are schedule to undergo the same or similar surgery as the requesting user may be identified.

Server 112 determines (1460) one or more corresponding attributes of the identified user to satisfy the threshold level of similarity. In some implementations, the threshold level of similarity may be an exact match with respect to one or more of the corresponding attributes. In an example, users that have undergone or are schedule to undergo the same medical procedure satisfy the threshold level of similarity. In other implementations, the threshold level of similarity may be less strict. In an example, users that have undergone or are scheduled to undergo a procedure to the same area of the requesting user's body may satisfy the threshold level of similarity. Other threshold levels of similarity are also possible, and other attributes may be used in the determination. In an example, age and/or gender of the requesting user and other users may be useful in determining a threshold level of similarity Server 112 transmits (1470), e.g., to a client device, information indicative of the identified user. In an example, information (e.g., information for a graphical user interface) can be transmitted to a client device 102 or 108 (FIG. 1). In some implementations, the information can be presented in one or more of the user interfaces 200-1300 described elsewhere in this specification. In some implementations, the transmitted information can specify that the identified user is a peer of the requesting user. In an example, the requesting user may want add the peer to the requesting user's list of peers so that the requesting user may track the recovery progress of the peer to improve the requesting user's own recovery.

Figure 15:
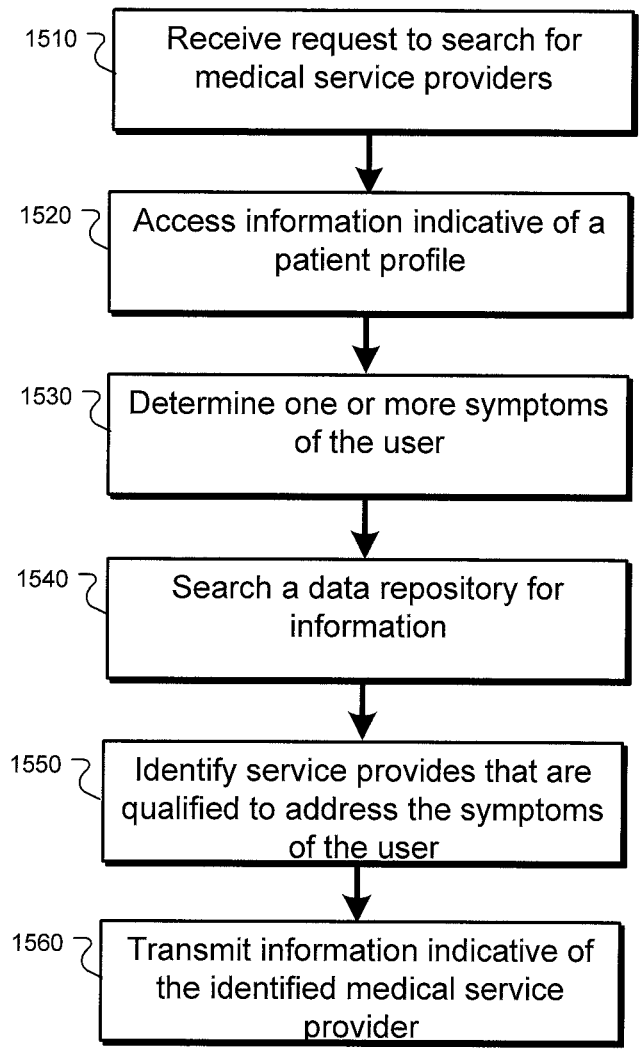
FIG. 15 is a flow chart of an example process that can be used to determine a medical service provide that can treat one or more medical symptoms of a requesting user.

FIG. 15 is a flow chart of an example process 1500 that can be used to determine a medical service provide that can treat one or more medical symptoms of a requesting user. In an example, server 112 implements process 1500. In general, the process 1500 uses symptoms of the requesting user of an online patient community system 100 (FIG. 1) to identify a qualified service provider that can treat the requesting user's symptoms 100. In general, process 1500 is described in relation to the online patient community system 100 that is configured to perform the process 1500, although other systems may be configured to perform process 1500.

In operation, server 112 receives (1510) a request to search medical service providers. In some implementations, the request can be received online patient community from a client device 102 or 108 (FIG. 1). In some implementations, the client device may be associated with a user of the online patient community system 100 (FIG. 1).

Server 112 accesses (1520) information indicative of a patient profile of the user, e.g., from data repository 114. In an example, profile information stored by the online patient community system 100 (FIG. 1) can be accessed. In some implementations, this profile information may include the age, gender, and other physical characteristics of the requesting user.

Server 112 determines (1530) one or more symptoms of the user. In some implementations, one or more symptoms can be included in the user profile. In other implementations, one or more symptoms can be determined based on certain other related information in the user profile. In an example, a user's age, smoking status, exercise status, and live feed updates pertaining to shortness of breath may be used to determine a lung-related symptom.

In an example, server 112 searches (1540) a data repository for information indicative of one or more medical service providers who are qualified to address at least one of the one or more symptoms of the user. In an example, the online patient community system 100 (FIG. 1) may maintain a database or other data repository that can be searched for information indicative of one or more medical service providers who are qualified to address at least one of the one or more symptoms of the user.

Server 112 identifies (1550) a medical service provider who is qualified to address at least one of the one or more symptoms of the user. In an example, medical service providers that are associated with treatment plans for one or more of the particular symptoms may identified as one of the one or more service providers that are qualified to address at least one of the one or more symptoms of the user. In some implementations, identifying one or more qualified service provide may include determining a number of top service providers that have higher outcome ratings relative to other service provides. In some implementations, identifying one or more qualified service provides may include determining a number of service providers that closest to the requesting user relative to other service providers. In some implementations, identifying one or more qualified service provides may include determining a number of service providers that can address more of the user's symptoms relative to other service providers.

Server 112 transmits (1560), e.g., to a client device, information indicative of the identified medical service provider. In an example, information can be transmitted to a client device 102 or 108 (FIG. 1). In some implementations, the information can be presented in one or more of the user interfaces 200-1300 described elsewhere in this specification.

Embodiments can be implemented in digital electronic circuitry, or in computer hardware, firmware, software, or in combinations thereof. An apparatus can be implemented in a computer program product tangibly embodied or stored in a machine-readable storage device for execution by a programmable processor; and method actions can be performed by a programmable processor executing a program of instructions to perform functions by operating on input data and generating output. The embodiments described herein, and other embodiments of the invention, can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Computer readable media for embodying computer program instructions and data include all forms of non-volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in special purpose logic circuitry. Any of the foregoing can be supplemented by, or incorporated in, ASICs (application-specific integrated circuits).

To provide for interaction with a user, embodiments can be implemented on a computer having a display device, e.g., a LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments can be implemented in a computing system that includes a back end component, e.g., as a data server, or that includes a middleware component, e.g., an application server, or that includes a front end component, e.g., a client computer having a graphical user interface or a Web browser through which a user can interact with an implementation of embodiments, or any combination of such back end, middleware, or front end components. The components of the system can be interconnected by any form or medium of digital data communication, e.g., a communication network. Examples of communication networks include a local area network (LAN) and a wide area network (WAN), e.g., the Internet.

The system and method or parts thereof may use the "World Wide Web" (Web or WWW), which is that collection of servers on the Internet that utilize the Hypertext Transfer Protocol (HTTP). HTTP is a known application protocol that provides users access to resources, which may be information in different formats such as text, graphics, images, sound, video, Hypertext Markup Language (HTML), as well as programs. Upon specification of a link by the user, the client computer makes a TCP/IP request to a Web server and receives information, which may be another Web page that is formatted according to HTML. Users can also access other pages on the same or other servers by following instructions on the screen, entering certain data, or clicking on selected icons. It should also be noted that any type of selection device known to those skilled in the art, such as check boxes, drop-down boxes, and the like, may be used for embodiments using web pages to allow a user to select options for a given component. Servers run on a variety of platforms, including UNIX machines, although other platforms, such as Windows 2000/2003, Windows NT, Sun, Linux, and Macintosh may also be used. Computer users can view information available on servers or networks on the Web through the use of browsing software, such as Firefox, Netscape Navigator, Microsoft Internet Explorer, or Mosaic browsers. The computing system can include clients and servers. A client and server are generally remote from each other and typically interact through a communication network. The relationship of client and server arises by virtue of computer programs running on the respective computers and having a client-server relationship to each other.

Other embodiments are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the invention.

What is claimed is:

1. A computer-implemented method, comprising:
receiving, by a processing device and from a client device associated with a requesting user of an online patient community, a request to search for other similar individual users who are associated with at least a threshold level of similarity to the requesting user;
accessing information indicative of a patient profile of the requesting user;
determining, based on contents of the patient profile, one or more attributes of the requesting user;
receiving from the requesting user a specification of which attributes of the requesting user are used as medical search criteria in searching for the similar individual user;
searching a data repository for information indicative of a user associated with one or more attributes corresponding to at least one of the medical search criteria specified by the requesting user;
identifying, based on searching, a user associated with one or more attributes corresponding to at least one of the medical search criteria specified by requesting user;
determining that the one or more corresponding attributes of the identified user satisfy the threshold level of similarity; and
transmitting, to the client device, information indicative of the identified user, with the transmitted information specifying the identified user as being a peer of the requesting user;
forming a direct social connection with one degree of separation, in a social networking platform of the online patient community, between (i) a user identity of the requesting user who specified which attributes are used as the medical search criteria, and (ii) a user identity of the identified, similar user.

2. The computer-implemented method of claim 1, further comprising:
receiving, from the client device, a request to connect the identified user to the requesting user in the online patient community.

3. The computer-implemented method of claim 1, further comprising:
receiving, from the client device, information indicative of one or more attributes of the requesting user; and
updating the patient profile of the requesting user with the information indicative of the one or more attributes.

4. The computer-implemented method of claim 1, further comprising:
accessing a medical data record of the requesting user;
parsing the medical data record;
determining, based on parsing, information indicative of one or more attributes of the requesting user; and
updating the patient profile of the requesting user with the information indicative of the one or more attributes.

5. The computer-implemented method of claim 1, further comprising:
receiving, from the client device, information indicative of recovery information of the requesting user; and
sharing the received recovery information with peers of the requesting user in the online patient community;
wherein the shared recovery information increases a speed of recovery of at least one of the peers of the requesting user, relative to other speeds of recovery that result from other shared information.

6. The computer-implemented method of claim 1, further comprising:
receiving, from the client device, information indicative of one or more of medical information of the requesting user; and
sharing the received medical information with peers of the requesting user in the online patient community.

7. An electronic system comprising:
one or more processing devices; and
one or more machine-readable hardware storage devices storing instructions that are executable to cause the one or more processing devices to perform operations comprising:
receiving, from a client device associated with a requesting user of an online patient community, a request to search for similar individual users who are associated with at least a threshold level of similarity to the requesting user;
accessing information indicative of a patient profile of the requesting user;
determining, based on contents of the patient profile, one or more attributes of the requesting user;
searching a data repository for information indicative of a user associated with one or more attributes corresponding to at least one of the one or more attributes of the requesting user;
receiving from the requesting user a specification of which attributes of the requesting user are used as medical research criteria in searching for the similar individual user;
searching a data repository for information indicative of a user associated with one or more attributes corresponding to at least one of the medical search criteria specified by the requesting user;
identifying, based on searching, a user associated with one or more attributes corresponding to at least one of the medical search criteria specified by the requesting user;
determining that the one or more corresponding attributes of the identified user satisfy the threshold level of similarity; and
transmitting, to the client device, information indicative of the identified user, with the transmitted information specifying the identified user as being a peer of the requesting user;
forming a direct social connection with one degree of separation, in a social networking platform of the online patient community, between (i) a user identity of the requesting user who specified which attributes are used as the medical search criteria, and (ii) a user identity of the identified, similar user.

8. The electronic system of claim 7, wherein the operations further comprise:
receiving, from the client device, a request to connect the identified user to the requesting user in the online patient community.

9. The electronic system of claim 7, wherein the operations further comprise:
receiving, from the client device, information indicative of one or more attributes of the requesting user; and
updating the patient profile of the requesting user with the information indicative of the one or more attributes.

10. The electronic system of claim 7, wherein the operations further comprise:
accessing a medical data record of the requesting user;
parsing the medical data record;

determining, based on parsing, information indicative of one or more attributes of the requesting user; and
updating the patient profile of the requesting user with the information indicative of the one or more attributes.

11. The electronic system of claim 7, wherein the operations further comprise:
receiving, from the client device, information indicative of recovery information of the requesting user; and
sharing the received recovery information with peers of the requesting user in the online patient community;
wherein the shared recovery information increases a speed of recovery of at least one of the peers of the requesting user, relative to other speeds of recovery that result from other shared information.

12. The electronic system of claim 7, wherein the operations further comprise:
receiving, from the client device, information indicative of one or more of medical information of the requesting user; and
sharing the received medical information with peers of the requesting user in the online patient community.

13. One or more machine-readable hardware storage devices storing instructions that are executable to cause one or more processing devices to perform operations comprising:
receiving, from a client device associated with a requesting user of an online patient community, a request to search for similar individual users who are associated with at least a threshold level of similarity to the requesting user;
accessing information indicative of a patient profile of the requesting user;
determining, based on contents of the patient profile, one or more attributes of the requesting user;
receiving from the requesting user a specification of which attributes of the requesting user are used as medical search criteria in searching for the similar individual user;
searching a data repository for information indicative of a user associated with one or more attributes corresponding to at least one of the medical search criteria specified by the requesting user;
identifying, based on searching, a user associated with one or more attributes corresponding to at least one of the medical search criteria specified by the requesting user;
determining that the one or more corresponding attributes of the identified user satisfy the threshold level of similarity; and
transmitting, to the client device, information indicative of the identified user, with the transmitted information specifying the identified user as being a peer of the requesting user;
forming a direct social connection with one degree of separation, in a social networking platform of the online patient community, between (i) a user identity of the requesting user who specified which attributes are used as the medical search criteria, and (ii) a user identity of the identified, similar user.

14. The one or more machine-readable hardware storage devices of claim 13, wherein the operations further comprise:
receiving, from the client device, a request to connect the identified user to the requesting user in the online patient community.

15. The one or more machine-readable hardware storage devices of claim 13, wherein the operations further comprise:
receiving, from the client device, information indicative of one or more attributes of the requesting user; and
updating the patient profile of the requesting user with the information indicative of the one or more attributes.

16. The one or more machine-readable hardware storage devices of claim 13, wherein the operations further comprise:
accessing a medical data record of the requesting user;
parsing the medical data record;
determining, based on parsing, information indicative of one or more attributes of the requesting user; and
updating the patient profile of the requesting user with the information indicative of the one or more attributes.

17. The one or more machine-readable hardware storage devices of claim 13, wherein the operations further comprise:
receiving, from the client device, information indicative of recovery information of the requesting user; and
sharing the received recovery information with peers of the requesting user in the online patient community;
wherein the shared recovery information increases a speed of recovery of at least one of the peers of the requesting user, relative to other speeds of recovery that result from other shared information.

18. The one or more machine-readable hardware storage devices of claim 13, wherein the operations further comprise:
receiving, from the client device, information indicative of one or more of medical information of the requesting user; and
sharing the received medical information with peers of the requesting user in the online patient community.

\* \* \* \* \*

UNITED STATES PATENT AND TRADEMARK OFFICE
CERTIFICATE OF CORRECTION

PATENT NO.        : 9,256,645 B2                                          Page 1 of 1
APPLICATION NO.   : 13/968046
DATED             : February 9, 2016
INVENTOR(S)       : Ali Adel Hussam It is certified that error appears in the above-identified patent and that said Letters Patent is hereby corrected as shown below:

Col. 21, line 8, claim 1, delete "other similar" and insert -- similar --

Col. 21, line 25, claim 1, delete "by" and insert -- by the --

Col. 22, line 24-27, claim 7, below "user;" delete "searching a data repository for information indicative of a user associated with one or more attributes corresponding to at least one of the one or more attributes of the requesting user;"

Col. 22, line 30, claim 7, delete "research" and insert -- search --

Signed and Sealed this
Third Day of May, 2016

Michelle K. Lee
*Director of the United States Patent and Trademark Office*